US012393725B2

(12) United States Patent
Medeiros et al.

(10) Patent No.: US 12,393,725 B2
(45) Date of Patent: Aug. 19, 2025

(54) HYGIENE COMPLIANCE DATA CHANNEL

(71) Applicant: Advanced Input Systems, Coeur d'Alene, ID (US)

(72) Inventors: Benjamin John Medeiros, Coeur d'Alene, ID (US); Mitchell S. Butzer, Coeur d'Alene, ID (US); Bret Thomas Stewart, Rathdrum, ID (US); Brett Harned, Coeur d'Alene, ID (US); Darrell Lee Janke, Spokane Valley, WA (US)

(73) Assignee: Advanced Input Systems, Coeur d'Alene, ID (US)

( * ) Notice: Subject to any disclaimer, the term of this patent is extended or adjusted under 35 U.S.C. 154(b) by 48 days.

(21) Appl. No.: 18/060,186

(22) Filed: Nov. 30, 2022

(65) Prior Publication Data

US 2023/0169206 A1    Jun. 1, 2023

Related U.S. Application Data

(60) Provisional application No. 63/284,259, filed on Nov. 30, 2021.

(51) Int. Cl.
*G06F 21/62* (2013.01)
*G16H 40/20* (2018.01)
(52) U.S. Cl.
CPC ......... *G06F 21/6245* (2013.01); *G16H 40/20* (2018.01)

(58) Field of Classification Search
CPC .......................... G06F 21/6245; G16H 40/20
See application file for complete search history.

(56) References Cited

U.S. PATENT DOCUMENTS

| 2012/0158419 | A1* | 6/2012 | Nuthi | G16H 40/20 705/2 |
| 2018/0048674 | A1* | 2/2018 | Black | H04L 63/02 |
| 2020/0193798 | A1* | 6/2020 | Lindstrom | G09B 19/003 |
| 2020/0250955 | A1* | 8/2020 | Goldfain | G16H 40/20 |
| 2020/0250956 | A1* | 8/2020 | Hayes | G08B 21/245 |
| 2021/0034724 | A1* | 2/2021 | Fong | G06V 40/25 |
| 2021/0295673 | A1* | 9/2021 | Liu | G16H 50/80 |
| 2021/0350689 | A1* | 11/2021 | Kelly | G08B 21/245 |
| 2022/0122448 | A1* | 4/2022 | Yegavolla | G06V 20/52 |

* cited by examiner

*Primary Examiner* — Kambiz Zand
*Assistant Examiner* — Afaq Ali
(74) *Attorney, Agent, or Firm* — Lee & Hayes, P.C.

(57) ABSTRACT

A method of securing sensitive data and hygiene compliance data may include receiving a first input and determining whether the first input is associated with a cleaning instance of one or more portions of a computing device. Based at least in part on the first input is not associated with a cleaning instance, the method may further include transmitting first data to a first computing system via a first communication channel. Based at least in part on the first input is associated with a cleaning instance, the method may further include transmitting second data to a second computing system via a second communication channel different from the first communication channel.

20 Claims, 8 Drawing Sheets

HYGIENE COMPLIANCE DATA CHANNEL

RELATED APPLICATIONS

This application claims priority to and incorporates U.S. Provisional Patent Application 63/284,259, filed Nov. 30, 2021, entitled "Hygiene Compliance Data Channel," in its entirety by reference.

BACKGROUND

Compliance with hygiene protocols has been an important consideration in many environments, such as in medical facilities. For example, a computing device and/or a medical tool located in a hospital room or medical office may be used by many different people on a medical staff. A hygiene protocol associated with the medical facility may mandate that the computing device and/or the medical tool be cleaned between uses and/or at a periodic interval. In existing technologies, the computing device and/or the medical tool may include alert systems to inform an individual on the medical staff that a cleaning in necessary. In some instances, data associated with a cleaning instance may be processed by the computing device and/or a computer associated with the medical tool and sent to a central computing system. The central computing system may be configured to process patient data and other sensitive information and may also function as a centralized hygiene monitoring system. The central computing system may process sensitive data as well as non-sensitive, hygiene compliance data. However, sending sensitive data concurrently with or in a same channel as non-sensitive data that is processed by an independent hygiene system may render the sensitive data vulnerable to attack and discovery of sensitive information by an unauthorized individual.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

DETAILED DESCRIPTION

Figure 1:
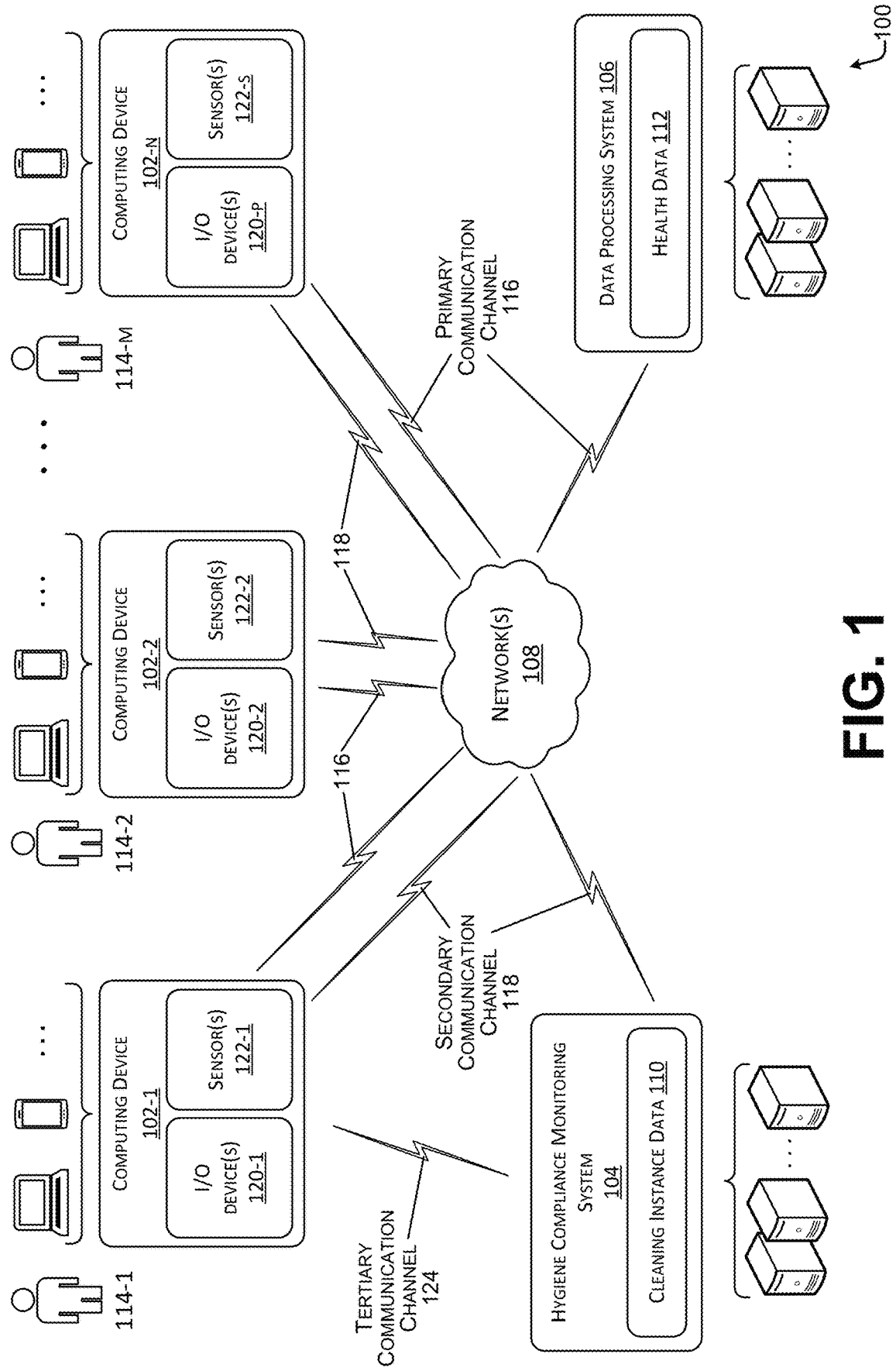
FIG. 1 is a schematic view of an example system usable to implement secure hygiene compliance monitoring, as described herein.

This application describes techniques for providing hygiene compliance data associated with a computing device to a hygiene compliance monitoring system via a hygiene compliance data communication channel that is separate from a communication channel associated with other data input via the device. In one example, the computing device may include an input/output device ("I/O device") or piece of hardware configured to communicate with data processing system via a first communication channel and with a hygiene compliance monitoring system via a second communication channel that is separate from and independent of the first communication channel and the data processing system. The first communication channel may include a wired and/or wireless connection to the data processing system. The second communication channel may include a wired and/or wireless connection to the hygiene compliance monitoring system.

In one example, the first communication channel may include a first pathway or communication connection with the data processing system. The first communication channel may include a pathway for user-generated data (e.g., data typed via a keyboard, mouse clicks to select data, etc.) to be transmitted to the data processing system and/or additional computing devices, storage systems, and/or the like. In one example, at least a portion of the user-generated data may include sensitive data, such as data that is protected under laws and/or regulations (e.g., Health Insurance Portability and Accountability Act, customer information, employee data, intellectual property, personal identifying information, etc.).

In one example, the second communication channel may include a second pathway or direct connection with the hygiene compliance monitoring system. The second communication channel may include a pathway for cleaning instance data associated with the I/O device of the computing device that is independent of the first communication channel. The cleaning instance data may include data associated with cleaning instances corresponding to the computing device. Non-limiting examples of cleaning instance data include times associated with the cleaning instance (start time, stop time, etc.), location associated with the cleaning instance, a user associated with the cleaning instance, percentage of surface cleaned, satisfaction (or not) of criteria associated with a cleaning instance (e.g., level of moisture, pressure, etc. satisfies one or more thresholds, percentage of surface cleaned satisfies a threshold, etc.), and/or the like. In one example, the computing device may provide, to the hygiene compliance monitoring system, a device identifier associated with the computing device, such as to enable the hygiene compliance monitoring system to identify the particular device associated with the cleaning instance.

In one example, the computing device may include one or more sensors configured to identify a cleaning instance and provide data associated therewith to the hygiene compliance monitoring system. Non-limiting examples of sensor(s) include pressure sensors, conductive sensors (e.g., conductive probes), capacitance sensors, humidity sensors, ultra-violet (UV) sensors, and/or the like. In one example, the sensor(s) may detect input associated with interaction with the computing device and may provide the input to the computing device. The computing device may include one or more processors configured to identify a cleaning instance associated with the interaction, such as from a detected amount of moisture on a surface of the I/O device (e.g., moisture associated with a cleaning wipe), detected movement associated with a cleansing gesture, and/or the like.

In one example, the computing device may be configured to identify the cleaning instance based in part on a direct input from a user of the cleaning instance (e.g., user presses a button to indicate a cleaning instance is complete, etc.). For example, a user interface of the computing device may include a cleaning verification button that, when pressed for a threshold amount of time (e.g., 3 seconds, 5 seconds, etc.) identifies that a cleaning instance is complete. In one example, the computing device may additionally be configured to identify the cleaning instance based in part on additional data received from one or more additional sensors. The additional sensor(s) may include microphones, image capture devices (e.g., still frame and/or video images), and/or the like that are configured to capture the additional data in an environment of the computing device and provide the additional data to the computing device. In one example, the additional sensor(s) may be associated with the computing device (e.g., a part of the computing device as separate sensors) and/or may be remote sensors (e.g., independent of the computing device). In one example, the additional sensors may be configured to provide the additional data to the computing device via a third communication channel, such as via a wired and/or wireless connection.

In one example, the computing device may be configured to process the data and/or the additional data to determine cleaning instance data associated with a cleaning instance. As described herein, the cleaning instance data may include a time, location, and/or user associated with a particular cleaning instance. The computing device may be configured to determine a time, location, and or a user associated with a cleaning instance. For example, the computing device may be coupled to a card reader associated with the computing device and may determine, based on an identification card input into the card reader, that a particular user is currently using the computing device and/or an associated computing device. The computing device may thus associate the particular user with a cleaning instance identified during a use session in which the identification card associated with the user is in the card reader. For another example, the computing device may receive input associated with a password or authentication code associated with a particular user and may be configured to identify the particular user based on the password or authentication code.

In one example, the computing device may be configured to process the data and/or the additional data to determine one or more characteristics associated with a cleaning instance. The characteristics may include a percentage of a surface of the computing device cleaned (e.g., percentage of the computing device that detects moisture, percentage of the surface that is depressed in a cleaning action, etc.), a level of moisture, pressure, etc. associated with the cleaning instance, a period of time associated with the cleaning instance, satisfaction (or not) of criteria associated with a cleaning instance (e.g., level of moisture, pressure, etc. satisfies one or more thresholds, percentage of surface cleaned satisfies a threshold, period of time satisfies a threshold, etc.), and/or the like. In one example, the computing device may be configured to determine whether the criteria associated with the cleaning instance is satisfied. Based on a determination that the criteria are satisfied, the computing device may be configured to provide an indication thereof to the user associated with the cleaning instance. For example, in response to determining criteria associated with a cleaning instance is satisfied, the computing device may cause a light (e.g., a light emitting diode (LED)) of the computing device to illuminate indicating a satisfactory cleaning instance.

In one example, the computing device may be configured to determine the satisfaction of criteria associated with the cleaning instance based on characteristics of cleaning materials. The computing device may be configurable to determine one or more thresholds associated with a cleaning instance based on a type, brand, make, and/or the like of cleaning material that is used. The computing device may receive input, such as during a set-up or initialization process, an update after initialization, and/or the like, associated with the cleaning materials, and may determine satisfaction of the thresholds based on the input. For example, a first computing device associated with a first user interface located in a first hospital may receive an input indicating that a first brand of cleaning wipe is used. Further, a second computing device associated with a second user interface located in a second hospital may receive an input indicating that a second brand of cleaning wipe is used. The first computing device may establish first thresholds associated with the first brand of cleaning wipe and the second computing device may establish second thresholds associated with the second brand of cleaning wipe that are different from the first thresholds.

In one example, the computing device may include a training model configured to train a threshold determination system associated with a user interface of the computing device. The threshold determination system may associate one or more thresholds with the user interface of the computing device, such as to determine whether a cleaning instance was satisfactory. As described herein, the thresholds may be associated with moisture level, pressure applied, time associated with a cleaning instance, and/or the like. In one example, the training model may receive, as an input one or more inputs associated with a training cleaning instance. In one example, the training model may be configured to receive the input and identify one or more thresholds (e.g., moisture level, capacitance detected, time associated with the capacitance, time of decay of capacitance, pressure detected, etc.) based on the input. The training model may then set the thresholds associated with a satisfactory cleaning instance based on the input.

Techniques described herein may improve a functioning of the computing device. In existing technologies, a hygiene compliance monitoring system may be associated with the I/O device of a computing device and may send cleaning data concurrently with and via a same channel as other data, such as sensitive or protected data. Such technologies may require the installation and maintenance of custom software on all computing devices within a facility. Each individual computing device may include an instance of cleaning monitoring software that must be continually updated. The installation and updates of each individual endpoint may require significant time and computing resources for each associated computing device. Unlike these conventional systems, the techniques described herein provide for hygiene compliance monitoring via separate, independent computing systems associated with the computing devices, that are configured to send data via a secondary communication channel (e.g., a second communication channel) that is separate and apart from a primary channel (e.g., a first channel) configured for transmission of sensitive data. At least because the independent computing system for hygiene compliance data (e.g., the I/O device processor) are not associated with the endpoints (e.g., the primary computing device), the techniques described herein require fewer computing resources from the associated primary computing device to initiate and/or maintain cleanliness monitoring functionality. As such, the techniques described herein improve the functioning of a computing device.

Additionally, the techniques described herein improve the security of sensitive data and/or other data input via the computing devices such as data that is protected under laws and/or regulations (e.g., Health Insurance Portability and Accountability Act (HIPA Act), customer information, employee data, intellectual property, personal identifying information, etc.). As described herein, in conventional systems, sensitive data and hygiene compliance data may be sent via a single communication channel such as via an endpoint associated with the computing devices. However, the hygiene compliance data sent via the single communication channel may not be subject to as strict compliance rules and security as the sensitive data. As such, to attack the sensitive data, a malicious actor may use the hygiene compliance data as a less secure entry point to access the sensitive data. Unlike these conventional systems, the systems and methods described herein enable the transmission of sensitive data via a first communication channel and the transmission of hygiene compliance data via a second communication channel that is different from the first communication channel (e.g., independent, separate, etc.). In one example, the second communication channel may include a secure communication channel with an associated level of security that is less than a heightened level of security associated with the first communication channel such as that used to enhance protection of the sensitive data. As such, a malicious actor may be precluded from accessing the sensitive data via an entry point associated with the hygiene compliance data. Accordingly, the techniques described herein may improve the security of sensitive data input via a computing device that may be subject to hygiene compliance monitoring protocols (e.g., cleanliness protocols).

These and other aspects are described further below with reference to the accompanying drawings. The drawings are merely an example implementation and should not be construed to limit the scope of the claims. For example, while examples are described primarily in the context of a medical environment (e.g., hospital, doctor's office, etc.), the techniques may be implemented in many other types of environments, such as in day care centers, schools, gymnasiums, fitness centers, casinos, call centers, and/or any other environment in which cleaning protocols are mandated and/or maintained.

Exemplary Embodiments

FIG. 1 is a schematic view of an example computing system 100 usable to implement example techniques described herein to enable cleaning instance data associated with one or more computing devices 102-1, 102-2, . . . 102-N, where N is any integer greater than or equal to 1 (collectively referred to herein as computing device(s) 102 unless specifically addressed otherwise) to be provided to a hygiene compliance monitoring system 104 via an independent communication channel. Each of the computing devices 102 may be operated and/or interacted with by a respective user 114-1, 114-2, 114-M, where M is any integer greater than or equal to 1 (collectively referred to herein as user(s) 114 unless specifically addressed otherwise). The hygiene compliance monitoring system 104 may include a computing system that is external to, and communicatively coupled with the computing devices 102. In one example, the computing devices 102 may include input/output (I/O) devices 120-1, 120-2, 120-P, where P is any integer greater than or equal to 1 (collectively referred to herein as I/O device(s) 120 unless specifically addressed otherwise) associated with computing devices 102. In one example, the computing devices 102 may include desktop computers, laptop computers, tablet computers, mobile devices (e.g., smart phones or other cellular or mobile phones, mobile gaming devices, portable media devices, etc.), or other suitable computing devices configured with the I/O device(s) 120. Though described primarily as being associated with a local computing device, the present systems and methods are not intended to be so limiting, and the computing devices 102 may additionally or alternatively be connected to a data processing system 106 configured to receive and process data input via the computing devices 102. For example, the computing devices 102 may include a medical implement or device configured to detect data associated with a patient and transmit the data to a remote data processing system 106 for processing.

In one example, the computing devices 102 may be configured to transmit two or more data streams over one or more networks 108. In one example the first data stream is sent over the primary communication channel 116, and the second data stream is sent over the secondary communication channel 118. In one example, the network(s) 108 may represent a collection of one or more networks such as, for example, the Internet, a corporate intranet, a virtual private network (VPN), a local area network (LAN), a wireless local area network (WLAN), a cellular network, a wide area network (WAN), a metropolitan area network (MAN), personal area network (PAN) (e.g., Bluetooth® low energy) and/or the like) over which the computing devices 102 may transmit cleaning instance data 110 to a hygiene compliance monitoring system 104 and/or health data 112 and/or other data to a data processing system 106. In one example, the networks 108 include two distinct and independent networks, one for each data stream, such as a first network and a second network. Stated another way, in one example, a first network 108 may be dedicated for the primary communication channel 116, and a second network 108 may be dedicated for the secondary communication channel 118 such that the primary communication channel 116 and the secondary communication channel 118 extend through entirely separate networks 108.

In one example, the computing devices 102 may be configured to transmit cleaning instance data 110 to the hygiene compliance monitoring system 104 via a first network 108 (e.g., a PAN) and health data 112 and/or other data to a data processing system 106 via a second network 108 (e.g., Internet, etc.). In such an example, the first network and the second network may be separate and independent of one another, such that data transferred via first network is not accessible via the second network, and vice versa.

As described herein, the computing devices 102 may include I/O device(s) 120 associated with computing devices 102. The I/O device(s) 120 may include keyboards, mice, touchpads, joysticks, trackballs, touchscreens and/or other on-screen controllers and/or any other device configured to provide data to an associated computing device 102. In one example, the computing devices 102 may include commercial off-the shelf devices that are configured with hardware and/or software to perform the functionalities described herein. In one example, the computing devices 102 may include devices with built-in hardware and/or software associated with performing the functionalities described herein. For example, each computing device 102 may include an I/O device 120 including at least a processor, computer-readable media, and a communication interface to enable communications (e.g., of cleaning instance data 110) via a secondary communication channel 118 (e.g., a second communication channel) in addition to a communication interface to enable communications (e.g., health data 112) via a primary communication channel 116 (e.g., a first channel).

Additionally, each of the computing devices 102 may include one or more sensor(s) 122-1, 122-2, 122-s, where s is any integer greater than or equal to 1 (collectively referred to herein as sensor(s) 122 unless specifically addressed otherwise) configured to detect a change in the environment in and around the computing devices 102 and provide sensor data to the I/O device 120 of a respective computing device 102. In one example, the change in the environment detected by the sensor(s) 122 may include a detection of a cleaning instance, such as when a first user 114-1 cleans a surface of a first computing device 102-1. Non-limiting examples of sensor(s) include pressure sensors, conductive sensors (e.g., conductive probes), capacitance sensors, humidity sensors, UV sensors, and/or the like. For example, the sensor(s) may detect moisture on the surface of the computing device 102 and may send sensor data associated with the detected moisture to the I/O device 120 of the computing device 102. The I/O device 120 may then process the sensor data to determine whether a cleaning instance occurred. Further, for example, the sensor(s) 122 may detect an amount of UV light emitted in an environment of the computing device 102, such as by a user 114 or a robot configured to emit UV light for killing microbes, germs, bacteria, and/or the like, and provide the sensor data associated with the detected UV light to the I/O device 120. The I/O device 120 may then process the sensor data to determine whether a cleaning instance occurred with respect to the computing device 102.

In one example, the I/O device 120 of a computing device 102 may be configured to identify the cleaning instance based in part on a direct input from a user 114 indicating the cleaning instance. For example, a user 114 may press an analog or digital button via a user interface of the computing device 102 to indicate a cleaning instance is complete, among other user inputs. For example, the computing device 102 may include a clean verification button that, when pressed for a threshold amount of time (e.g., 3 seconds, 5 seconds, etc.) identifies that a cleaning instance is complete. In one example, the I/O device 120 may additionally be configured to identify the cleaning instance based in part on additional data received from one or more additional sensor(s) associated with the sensor(s) 122. The additional sensor(s) may include microphones, image capture devices (e.g., still frame and/or video images), and/or the like that are configured to capture the additional data in an environment of the computing device 102 and provide the additional data to the I/O device 120 of the computing device 102. In one example, the additional sensor(s) may be associated with the computing device 102 (e.g., a part of the computing device 102 as separate sensor(s) 122) and/or may be remote sensors (e.g., independent of the I/O device 120 of the computing device 102). In one example, the additional sensor(s) may be configured to provide the additional data to the I/O device 120 via a tertiary communication channel 124, such as via a wired and/or wireless connection. For example, a first computing device 102-1 may be associated with an attached camera that is configured to provide image data to the I/O device 120 via a wireless connection. The I/O device 120 may receive the image data and determine whether a cleaning instance occurred. In one example, the additional image data may supplement sensor data received from the sensor(s) 122, such as to ensure that the cleaning instance satisfied one or more criteria associated with a cleaning instance (e.g., a satisfactory amount of cleaning occurred).

In one example, the I/O device 120 may be configured to process the data and/or the additional data obtained from the sensor(s) 122 to determine or generate cleaning instance data 110 associated with a cleaning instance. As described herein, the cleaning instance data 110 may include a time, location, and/or user 114 associated with a particular cleaning instance. The I/O device 120 may be configured to determine a time, location, and or a user 114 associated with a cleaning instance. For example, the I/O device 120 may be coupled to a card reader coupled to or included within the computing device 102 and may determine, based on an identification card input into the card reader, that a second user 114-2 is currently using a computing device 102-2 and/or associated computer. The I/O device 120-2 may thus associate the second user 114-2 with a cleaning instance identified during a use session in which the identification card associated with the user is in the card reader. In one example, the computing device 102-2 may receive input associated with user credentials (e.g., username, password, etc.) associated with the second user 114-2 and may be configured to identify the second user 114-2 based on the user credentials.

In one example, the I/O device 120 may be configured to receive user data from the associated computing device. In one example, the I/O device 120 may be coupled to the associated computing device, such as via a wired and/or wireless connection. Further, the I/O device 120 may be configured to receive data associated with a user identification. The second user 114-2 may input user credentials via the computing device 102-2, the user credentials may be verified by the associated computing device 102-2, and the associated computing device 102-2 may send an indication of the identified and verified user to the I/O device 120. In one example, the data transferred between the associated computing device 102-2 and the I/O device 120-2 may be limited to non-sensitive data, such as data associated with cleaning instances (e.g., a user identifier associated with a user 114), a cleaning protocol, and/or the like.

In one example, the hygiene compliance monitoring system 104 may be configured to push data to the I/O device 120 via the associated computing device(s). For example, the hygiene compliance monitoring system 104 may push software updates, cleaning protocol updates, and/or the like to the I/O device 120 via the associated computing device(s) 102. In one example, the hygiene compliance monitoring system 104 may be configured to ensure that the I/O device(s) 120 associated with the computing devices 102 are up to date and functioning properly as to the functions of the computing devices 102 as described herein.

In one example, the hygiene compliance monitoring system 104 may additionally or alternatively push updates and data to the I/O device(s) 120 via the secondary communication channel 118. In one example, the secondary communication channel 118 may be configured for two-way communications. In one example, the secondary communication channel 118 may be configured for one-way communication, such as from the computing device 102 to the hygiene compliance monitoring system 104. In one example, the hygiene compliance monitoring system 104 may push data to the I/O device 120 via a tertiary communication channel 124 that is different from the secondary communication channel.

As described herein, the I/O device 120 may be configured to transmit cleaning instance data 110 to the hygiene compliance monitoring system 104. The I/O device 120 may determine the cleaning instance data 110 based on the sensor data and/or additional data received from the sensor(s) 122 of the computing devices 102 and/or additional sensors in the environment such as, for example, additional sensors associated with the computing device 102 or located remotely in proximity to the computing device 102. In one example, the I/O device 120 may be configured to process the sensor data and the additional data and determine one or more characteristics associated with a cleaning instance. The characteristics may include a percentage of a surface of the computing device 102 cleaned. Sensor data defining the percentage of the surface of the computing device 102 cleaned may be determined via the sensor(s) 122. The characteristics may include, for example, a percentage of the computing device 102 at which moisture is detected by the sensor(s) 122. The characteristics may also include a percentage of the surface that is depressed based on human-machine interface input. For example, the percentage of the surface that is depressed may include a percentage of keys on a keyboard depressed, a number of keys of the keyboard that are depressed simultaneously or in a pattern associated with a cleaning instance, and combinations thereof. The characteristics may also include a level of moisture, pressure, etc. associated with the cleaning instance, a period of time associated with the cleaning instance, and satisfaction (or not) of criteria associated with a cleaning instance. The satisfaction (or not) of criteria associated with a cleaning instance may include, for example, a level of moisture, pressure, etc. that satisfies one or more thresholds. The characteristics may further include a percentage of the surface cleaned that satisfies a threshold and a period of time that satisfies a threshold. In one example, the characteristics may include a combination of the characteristics described herein and/or other characteristics.

In one example, the I/O device 120 may be configured to determine whether the criteria associated with the cleaning instance is satisfied. Based on a determination that the criteria are satisfied, the I/O device 120 may be configured to provide an indication thereof to the user 114 associated with the cleaning instance via, for example, a user interface of the computing device 102. For example, in response to determining criteria associated with a cleaning instance are satisfied, the I/O device 120 may cause a chime to be emitted from a speaker of the computing device 102 to indicate a satisfactory cleaning instance. As another example, in response to determining criteria associated with a cleaning instance are satisfied, the I/O device 120 may cause a notification to appear on a user interface of the computing device 102.

In one example, the I/O device 120 may be configured to determine the satisfaction of criteria associated with the cleaning instance based on characteristics of cleaning materials. The I/O device 120 may be configurable to determine one or more thresholds associated with a cleaning instance based on a type, brand, make, and/or the like of cleaning material that is used. The I/O device 120 may receive input, such as during a set-up or initialization process, an update after initialization, and/or the like, associated with the cleaning materials, and may determine satisfaction of the thresholds based on the input. As described above, the input may be received from the hygiene compliance monitoring system 104 via the associated computing device 102 and/or directly via a tertiary communication channel 124 between the hygiene compliance monitoring system 104 and the I/O device 120. For example, the tertiary communication channel 124 may include a communication channel that is separate from the primary communication channel 116 between the computing device 102 and the data processing system 106 and the secondary communication channel 118 between the computing device 102 and the hygiene compliance monitoring system 104 that is configured to transmit cleaning instance data 110. For example, a first I/O device 120-1 associated with a first computing device 102-1 located in a first gym facility may receive an input indicating that a first brand of cleaning wipe is used and a second I/O device 120-2 associated with a second computing device 102-2 located in a second gym facility may receive an input indicating that a second brand of cleaning wipe is used. The first I/O device 120-1 may establish first thresholds associated with the first brand of cleaning wipe and the second I/O device 120-2 may establish second thresholds associated with the second brand of cleaning wipe that are different from the first thresholds. In one example, the first computing device 102-1 and the second computing device 102-2 may be associated with exercise equipment, such as treadmills, stair climbers, ellipticals, stationary bicycles, rowers, and/or the like.

In one example, the I/O device 120 may include a training model configured to train a threshold determination system associated with the computing device 102. The threshold determination system may associate one or more thresholds with the computing device 102, such as to determine whether a cleaning instance was satisfactory. In one example, the thresholds may be associated with moisture level, pressure applied, time associated with a cleaning instance, and/or the like as described herein. In one example, the training model may receive one or more inputs associated with a training cleaning instance. In one example, the training model may be configured to receive the input(s) and identify one or more thresholds (e.g., moisture level, capacitance detected, time associated with the capacitance, time of decay of capacitance, pressure detected, etc.) based on the input(s). The training model may then set the thresholds associated with a satisfactory cleaning instance based on the input(s). For example, a user 114 may clean a surface of the computing device 102 to a satisfactory level as a training cleaning instance. The training model may receive sensor data and/or additional data associated with the training cleaning instance and may determine pressure thresholds, moisture thresholds, timing thresholds, and/or the like associated with the training cleaning instance. The training model may establish the determined threshold(s) as the thresholds for future cleaning instances, to determine whether a cleaning instance is satisfactory.

In one example, the sensor(s) 122 of the computing devices 102 may be configured to be field tested and/or calibrated by a user to ensure an accuracy of the sensor data derived from the activation of the sensor(s) 122. In one example, the testing and/or calibration may ensure that cleaning operations such as, for example, cleaning instances are detected and/or recorded accurately such as, for example, those cleaning instances that have been missed or not missed. In one example, the testing and/or calibration may additionally ensure that cleaning operations satisfy one or more cleaning criteria, such as those determined based on cleaning protocols. The cleaning protocols may be determined by a regulatory commission, a company or organization, an administrator, and/or the like. As described herein, in one example, a calibration may include a learning or training mode in which a computing device 102 is cleaned one or more times, to provide data associated with a satisfactory cleaning instance. The computing device 102 (e.g., I/O device 120) may be configured to establish one or more thresholds based on sensor data associated with the training cleaning instance(s).

Figure 2:
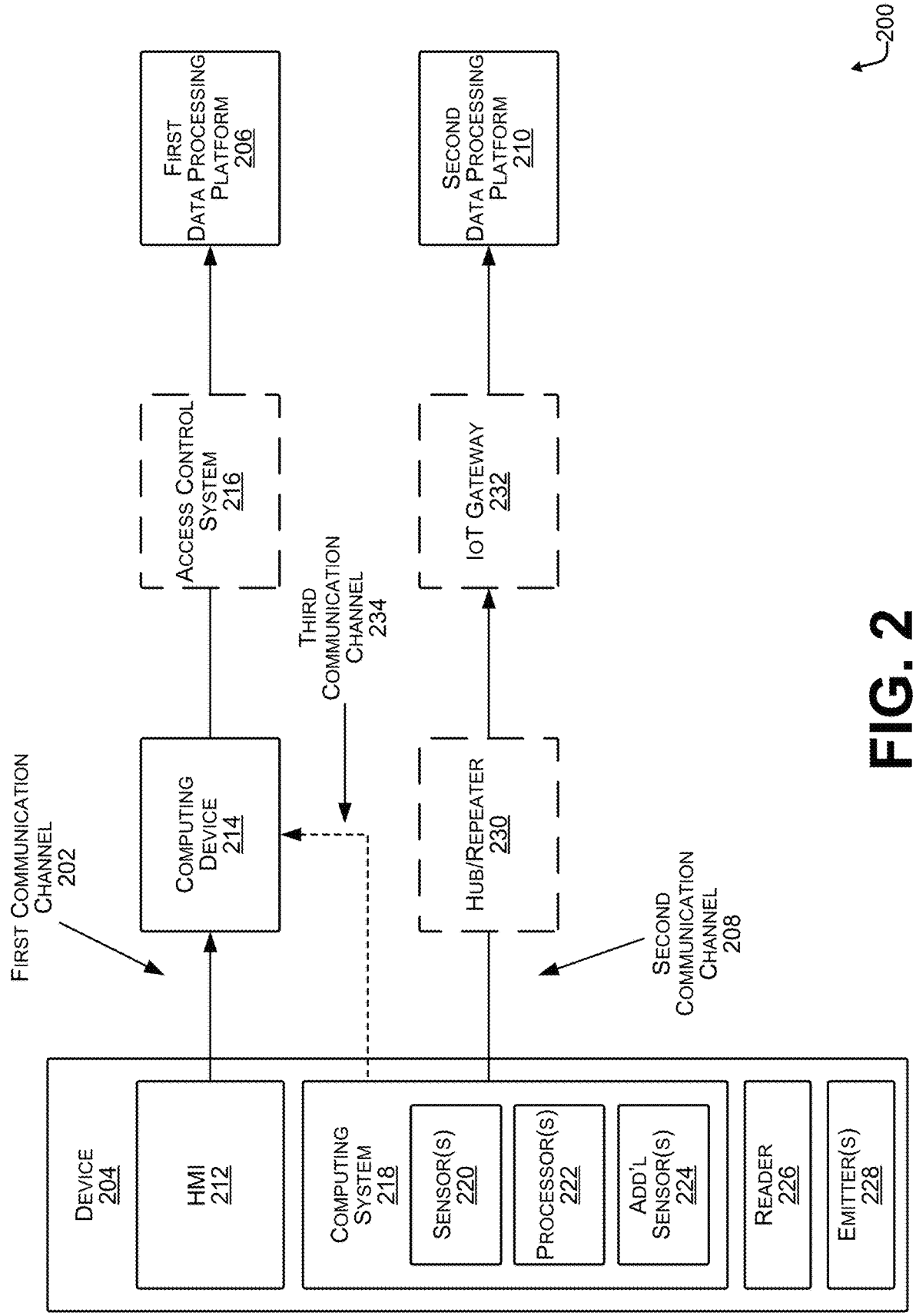
FIG. 2 is an example block diagram illustrating a primary channel configured for sensitive data and a secondary channel configured for hygiene compliance data, as described herein.

FIG. 2 is an example block diagram 200 illustrating a first communication channel 202 configured to transmit first data from a device 204, such as computing device 102 of FIG. 1, to a first data processing platform 206 and a second communication channel 208 configured to transmit second data from the device 204 to a second data processing platform 210. In one example, the first data may include sensitive data or other data input via the device 204 such as the health data 112 of FIG. 1 that is to be sent to a secure data processing system such as, for example, the data processing system 106 of FIG. 1. Further, in one example, the second data may include hygiene compliance data such as the cleaning instance data 110 of FIG. 1 that is sent to a hygiene compliance monitoring system such as, for example, the hygiene compliance monitoring system 104 of FIG. 1. Though described, in one example, as sensitive data, such as that associated with governmental laws, regulations, policies, and/or the like, this is not intended to be so limiting, and the data transmitted via the first communication channel 202 may include non-sensitive data, such as workout data in a fitness center environment, student data in a school environment, and/or the like. In one example, the transmission of hygiene compliance data via the second communication channel 208 that is independent of the first communication channel 202 may improve the security associated with the sensitive data and/or other data transmitted via the first communication channel 202. A malicious actor attempting to gain access to the sensitive data or other data transmitted via the first communication channel 202 to the first data processing platform 206 may be precluded from utilizing hygiene compliance monitoring system associated with the second communication channel 208, which may include different security protocols than those associated with sensitive data, to attempt to gain access to the sensitive data, as the systems and communication channels are separate and independent. As such, the techniques described herein may improve the safety and security of sensitive data input via the device 204.

As illustrated in FIG. 2, the first communication channel 202 may be configured to transmit first data to a first data processing platform 206, such as the data processing system 106 of FIG. 1. In one example, the data may be input by a user, such as user 114, into the device 204, which may be an I/O device associated with a computing device 214. In one example, the device 204 may include a human-machine interface (HMI) 212 configured to enable the user to interact with the associated computing device 214. As described herein, the HMI 212 may include a personal user interface including software that is configured to receive input via the device 204 (e.g., I/O device hardware), convert the user input into an electronic signal, and transmit the user input as the electronic signal to an associated computing device 214. The personal interface may include a personal touch interface configured to receive direct (e.g., touch) input from a user, a non-touch interface, such as that configured for visual input (e.g., associated with facial recognition, biometric scanning, gestures, etc.), audio input, or a combination of the foregoing (e.g., hybrid device). Though illustrated as separate components, this is not intended to be limiting, and it is understood that the device 204 may be incorporated into the computing device 214, as a component thereof. For example, the device 204 may include a touchscreen display associated with the computing device 214. In one example, an antimicrobial coating or other coating that reduces or eliminates microbes, germs, bacteria, and combinations thereof may be placed on the HMI 212.

In one example, the HMI 212 may send the input as first data (e.g., key codes, mouse clicks, selections, etc.) to the computing device 214 via the first communication channel 202. The first communication channel 202 may include a communication channel, as described herein, such as any wired and/or wireless network configured for data transmission. In one example, the computing device 214 may be associated with a first data processing platform 206, such as that associated with a centralized medical record system or the like. In one example, the computing device 214 may be configured to upload or otherwise send data input via the HMI 212 to the first data processing platform 206 for long term storage purposes, data analysis purposes, and similar purposes. For example, the computing device 214 may send the input to the first data processing platform 206 for storage in association with a medical record of a patient.

In one example, the computing device 214 may send the first data directly to the first data processing platform, such as via the first communication channel 202 and/or another channel configured to transmit sensitive data. In one example, the computing device 214 may send the first data to the first data processing platform 206 via an access control system 216. The access control system 216 may include a firewall, a gateway, a controller, an orchestrator, a manager, routers, switches, or other security system to prevent malicious actors from accessing the first (e.g., sensitive) data. In one example, the access control system 216 may include an intrusion detection system configured to identify attacks on one or more of the device 204, the first data processing platform 206, the computing device 214, and the first communication channel 202. The access control system 216 may provide a means by which the first data may further be protected from attack by malicious actors.

Additionally, the device 204 may include a computing system 218 (e.g., I/O device 120) configured to process second data associated with one or more cleaning instances of a surface of the device 204. As described herein, the cleaning instance may include a cleaning, by a user 114, utilizing one or more cleaning supplies, such as an antibacterial cleansing wipe, an anti-bacterial spray and rag, soap and water, a vinegar solution, and/or another substance configured to kill or otherwise neutralize pathogens, bacteria, microbes, and/or the like, in to clean and sanitize a surface of the device 204 according to one or more cleaning protocols. As described herein, the computing system 218 may include and/or be coupled to one or more sensors 220 configured to detect a change to an environment associated with the device 204. In one example, the sensor(s) 220 may be configured to identify a change to the environment of the device that is related to a cleaning instance, or a cleaning of the device 204 as described herein. Non-limiting examples of sensor(s) 220 may include pressure sensors, conductive sensors (e.g., conductive probes), capacitance sensors, humidity sensors, UV sensors, and/or the like. In one example, the sensor(s) 220 may detect input associated with an interaction with the device 204 and may provide the input to the computing system 218 as sensor data. The interaction may include a cleaning interaction, such as a cleaning instance, or another interaction, such as a spill of liquid, a touch of a wet hand, and/or the like, that does not constitute a cleaning instance. The computing system 218 may include one or more processors 222 configured to identify a cleaning instance associated with the interaction, such as from a detected amount of moisture on a surface of the device 204 (e.g., moisture associated with a cleaning wipe), detected movement associated with a cleansing gesture, and/or the like. Though illustrated as being separate from the HMI 212, it is understood that the processor(s) 222 and the HMI 212 may, in one example, share processors. In one example, the processor(s) 222 may be configured to perform functions described herein with regard to the HMI 212. In one example, such as when the device 204 includes an add-on to an existing I/O device, the processor(s) 222 may be independent of other processors associated with the HMI 212.

In one example, the computing system 218 may be configured to receive the sensor data and determine one or more characteristics associated with the interaction. The characteristics may include a percentage of a surface of the device 204 cleaned (e.g., percentage of the device 204 that detects moisture, percentage of the surface that is depressed (e.g., percentage of the total number of keys of a keyboard that are depressed), etc.), a level of moisture, pressure, etc. associated with the cleaning instance, a period of time associated with the cleaning instance, satisfaction (or not) of criteria associated with a cleaning instance (e.g., a level of moisture, a level of pressure, etc. that satisfies one or more thresholds, a percentage of surface cleaned that satisfies a threshold, a period of time that satisfies a threshold, etc.), and/or the like. For example, the computing system 218 may determine, based on a determination that a percentage of the keys of a keyboard are depressed, such as that determined based on input associated with the HMI 212, that a percentage of the keyboard was cleaned in a cleaning instance. In one example, the HMI 212 and/or the processor(s) 222 may be configured to identify input associated with a cleaning instance based on a determination that two or more keys are depressed simultaneously and/or consecutively, such as in a sweeping motion of a cleaning tool, implement, or cloth across the keys.

In one example, the computing system 218 may be configured to determine whether one or more criteria associated with the cleaning instance is satisfied. The computing system 218 may be configured to determine whether the interaction includes a cleaning instance based in part on the characteristic(s).

In one example, the computing system 218 may determine that the interaction does not satisfy one or more criteria associated with a cleaning instance. For example, the detected input may be associated with a coffee spill on a portion of the device 204. Based on a determination that the moisture sensed by the sensors 220 exceeds an amount of moisture associated with a cleaning instance and/or that the moisture is sensed in a portion of, and not across the entire device 204, the computing system 218 and the processor(s) 222 may determine that the interaction is not a cleaning instance. In one example, based on a determination that an instance of sensor data (e.g., sensor data received during a period of time) does not constitute a cleaning instance, the computing system 218 may determine to not provide the sensor data to the second data processing platform 210 as the second data. Based on a determination that a spill or other non-cleaning interaction occurs with the device 204, the computing system 218 may determine to withhold data associated therewith from the second data processing platform 210.

In one example, based on a determination that the cleaning interaction includes a cleaning instance based on a determination that an amount of moisture, a pressure, and/or an amount of surface associated with the cleaning instance satisfies one or more criteria (e.g., satisfies one or more threshold(s), etc.), the computing system 218 may identify the cleaning interaction as being a bona fide cleaning instance. As described herein, the computing system 218 may be configured to determine that the cleaning instance satisfies one or more criteria associated with a satisfactory cleaning based on sensor data from the sensor(s) 220 and/or the characteristic(s) associated therewith.

In one example, the computing system 218 may additionally or alternatively determine whether the cleaning instance satisfies criteria associated with a satisfactory cleaning based on additional data received from additional sensor(s) 224. The additional sensor(s) 224 may include microphones, image capture devices (e.g., still frame and/or video images), motion detectors, and/or the like that are configured to capture the additional data in an environment of the device 204 and provide the additional data to the computing system 218. In one example, the additional sensor(s) may detect a contaminating instance within the vicinity of the computing system 218 such as, for example, a sneeze by a user, a spilling of a fluid on the computing system 218 or another contaminating instance. In one example, the contaminating instance detected by the additional sensor(s) 224 may be used to trigger a notification to a user to begin a cleaning instance of the computing system 218.

Though illustrated as being associated with the device 204, such as a component thereof, it is understood that the additional sensor(s) 224 may additionally or alternatively include sensor(s) coupled to the device 204, such as by a wired and/or wireless connection, that are not associated with detecting cleaning data. The additional sensor(s) 224 may include additional sensor(s) of the device 204 and/or other sensors that are located in an environment of the device 204, such as in a same room, proximate or associated with the computing device 214, and/or the like. For example, the additional sensor(s) 224 may include a camera that is associated with the computing device 214 and configured to provide data to the computing system 218 of the device 204.

In one example, the additional sensor(s) 224 may be configured to provide the additional data to the computing system 218 via a third communication channel 234. Continuing the example from above in which the additional sensor(s) 224 includes a camera associated with the computing device 214, the additional sensor(s) 224 may be configured to provide image data to the computing system 218 via a wireless connection. The computing system 218 may receive the image data and determine whether a cleaning instance occurred. In one example, the additional image data may supplement sensor data received from the sensor(s) 220, such as to ensure that the cleaning instance satisfied one or more criteria associated with a cleaning instance (e.g., a satisfactory amount of cleaning occurred). In one example, the camera acting as the additional sensor(s) 224 may detect motion, images, or other data that identifies, for example, a user 114 at the device 204 and the activities the user 114 is engaging in including a cleaning instance, a utilization of the device 204, or other activity.

In one example, the computing system 218 may be configured to process the sensor data and/or the additional data and determine cleaning instance data associated with a cleaning instance. In one example, the computing system 218 may send the cleaning instance data to the second data processing platform 210 as second data. As described herein, the cleaning instance data may include a time, location, and/or a user 114 associated with a particular cleaning instance. In one example, the cleaning instance data may additionally include one or more characteristics of a cleaning instance. The characteristics may include a percentage of a surface of the device 204 cleaned (e.g., percentage of the device 204 that detects moisture, percentage of the surface that is depressed, etc.), a level of moisture, pressure, etc. associated with the cleaning instance, a period of time associated with the cleaning instance, satisfaction (or not) of criteria associated with a cleaning instance (e.g., level of moisture, pressure, etc. satisfies one or more thresholds, percentage of surface cleaned satisfies a threshold, period of time satisfies a threshold, etc.), and/or the like.

In one example, based on a determination that the criteria are satisfied (e.g., satisfactory cleaning instance occurred), the computing system 218 may be configured to provide an indication thereof to a user associated with the cleaning instance, such as via one or more emitters 228. Non-limiting examples of emitter(s) 228 may include a light, a speaker, a haptic device, a notification displayed on a user interface, and/or other device configured to emit light, sound, motion, and/or the like. For example, in response to determining criteria associated with a cleaning instance are satisfied, the computing system 218 may cause a light to be emitted via an emitter 228 such as an electromagnetic wave emitter (e.g., a light emitting diode (LED) for a period of time, to indicate a satisfactory cleaning instance. For another example, as described herein, the computing system 218 may be configured to provide an indication that a cleaning instance is required, such as based on a cleaning protocol. In such an example, the computing system 218 may cause a light to be emitted from the emitter 228 (e.g., LED, etc.) to indicate to a user that a cleaning of the device 204 is required. In response to determining a satisfactory cleaning instance, the computing system 218 may cause the emitter 228 to extinguish, change color, change a pattern of activation, or combinations thereof.

As described herein, the cleaning instance data may include a time, location, and/or user data associated with a user 114 corresponding to a cleaning instance. In one example, the computing system 218 may be configured to determine a time, location, and/or user data associated with the user 114 corresponding to the cleaning instance. In one example, the computing system 218 may identify the user associated with the cleaning instance based on data input via the device 204 and/or data provided by the computing device 214. For example, the computing system 218 may identify the user 114 based on user credentials input via the device 204 and/or provided to the device 204 by the associated computing device 214. In one example, the computing system 218 may identify the user based on data received from a reader 226 associated with the device 204. The reader 226 may include a radio-frequency identification (RFID) reader, a card reader, a code scanner, a biometric scanner, other types of identification devices, and combinations thereof that are configured to process an input access or identification code or card and identify a user 114 associated therewith. For example, the reader 226 may include a card reader configured to identify a user 114 associated with an identification card inserted therein or scanned thereby. As another example, the reader 226 may include a biometric scanner configured to detect a portion of a user's body (e.g., fingerprint, eyeball, face, etc.) and identify the user 114 based on the biometric scan.

In one example, based on an identification of a new user using the computing device 214 and/or the device 204, the computing system 218 may determine that a cleaning instance is necessary, such as based in part on a cleaning protocol. The computing system 218 may receive an indication that a new user is associated with the device 204 such as, for example, a logging into the computing device 214, inserted an identification card into the reader 226, and/or other indication. The computing system 218 may determine, based on a cleaning protocol, that a cleaning instance is necessary. In one example, the computing system 218 may be programmed with cleaning protocol data. The computing system 218 may store the cleaning protocol data in a datastore. The cleaning protocol data may include instructions associated with the cleaning protocol. For example, the cleaning protocol data may include a first instruction to clean the device 204 when a new user is associated with the device 204 and/or the computing device 214, a second instruction to clean the device 204 at a periodic interval (e.g., every hour, every four hours, etc.), a third instruction to clean when a threshold amount of dust or particulates are measured on a surface of the device 204 and/or in the air (e.g., measured by one or more sensors 220 and/or additional sensor(s) 224), other instructions, and combinations thereof. In one example, the computing system 218 may be programmed to determine a dirty state of the device 204, such as when a threshold amount of dust, particulates, and/or the like are on or proximate to the device 204. In one example, the computing system 218 may be configured to provide an indication to a user, such as via the emitter 228, that a cleaning instance is necessary. In one example, the detection of a dirty state and indication thereof to a user may be associated with a cleaning protocol. The cleaning protocol may include a periodic cleaning requirement as well as intermittent cleaning requirements based on conditions detected on a surface of the device 204 and/or in the environment of the device 204.

In one example, the computing system 218 may receive the cleaning protocol data from the second data processing platform 210 via an independent channel or network that is separate from the second communication channel 208. The second data processing platform 210 may be coupled to the computing system 218 via an additional channel or network configured to transmit cleaning protocol data. In one example, the computing system 218 may receive the cleaning protocol data from the computing device 214 via the first communication channel 202 or an additional or alternate channel between the computing system 218 and the computing device 214. The first communication channel 202 and/or the other channel may be configured to transmit cleaning protocol data to the computing system 218.

In one example, in response to identifying an interaction with the device 204, such as a cleaning instance associated therewith, the computing system 218 may send the cleaning instance data as second data to the second data processing platform 210 via the second communication channel 208. In one example, the second communication channel 208 may include a channel configured for transmission of data between the device 204 and the second data processing platform 210. In one example, the second communication channel 208 may include a one-way data channel or a two-way data channel.

In one example, the second channel may include a personal area network communication channel including an IEEE 802.15 standard such as, for example, Bluetooth® low energy and/or the like. In one example, the computing system 218 may optionally send the second data to the second data processing platform 210 via a hub/repeater 230. The hub/repeater 230 may be configured to receive instances of second data (e.g., cleaning instance data) from one or more devices 204 (e.g., computing devices 102, FIG. 1) such as in data packets, and transmit the instances of second data to the second data processing platform 210. In one example, the hub/repeater 230 may be configured to re-transmit a signal including the second data, such as to enable the second data to travel a further distance than that enabled by the computing system 218. In one example, the hub/repeater 230 may re-transmit the second data at a higher or lower power, amplitude, frequency, and/or the like, such as to send the second data to the second data processing platform 210 located a distance away from the device(s) 204 and/or the hub/repeater 230.

In one example, the hub/repeater 230 may be associated with a first device 204 communicatively coupled to a plurality of devices. In such an example, the hub/repeater 230 may receive data from the first device 204 and/or other devices 204 of the plurality of devices and may be configured to re-transmit the cleaning instance data, such as to the second data processing platform 210. In one example, the first device 204, acting as the parent device associated with the other, child, devices 204, may include increased power functionalities (e.g., larger, more powerful batteries, additional or enhanced Ethernet connections, etc.) to enable the functionalities of the hub/repeater 230.

In one example, the computing system 218 and/or the hub/repeater 230 may optionally send (e.g., re-transmit) the second data to the second data processing platform 210 via an Internet of Things (IoT) gateway 232. The IoT gateway 232 may include a platform (e.g., hardware, software, etc.) configured to connect one or more devices (e.g., devices 204, hub/repeater 230, etc.) to the second data processing platform 210, such as that stored and/or operating in a cloud network environment. In one example, the IoT gateway 232 may be configured to aggregate cleaning instance data (e.g., second data) from one or more device(s) 204 and send the aggregated cleaning data to the second data processing platform 210.

Though illustrated as a component separate from the device 204, in one example, the IoT gateway 232 may be a component of the device 204 itself. In one example, the IoT gateway 232 may be configured to receive data processed by the computing system 218 and transmit the second data directly to the second data processing platform 210, such as via a Wi-Fi network or other network. In one example, the device 204 may be configured to transmit the second data (e.g., the cleaning instance data) to the second data processing platform 210 (e.g., cleanliness monitoring system), via the Internet separate and apart from the first communication channel 202.

In one example, the second data processing platform 210 may be configured to receive the second data and store the second data in one or more datastores. In one example, the second data processing platform 210 may be configured to process the second data, such as to determine and/or verify that a satisfactory cleaning instance has occurred (e.g., detect a clean state of the device 204). In one example, the second data processing platform 210 may receive raw sensor data and cleaning instance data. The second data may include cleaning instance data, such as the time, location, user data, characteristic(s), an indication of whether the cleaning instance was satisfactory, and/or the like. Further, the second data may include the raw sensor data from the sensor(s) 220 and/or the additional sensor(s) 224. In one example, the second data processing platform 210 may be configured to determine, based on the second data, that a satisfactory cleaning instance occurred, such as utilizing the techniques described above with respect to the computing system 218. For example, the second data processing platform 210 may compare the sensor data to one or more thresholds. In one example, the second data processing platform may be configured to send a verification and/or indication of the satisfactory cleaning instance to the computing system 218, such as via a third communication channel 234 that is separate and independent of (e.g., different from) the second communication channel 208 and/or the first communication channel 202. In one example, the computing system 218 may receive the verification and/or indication of the satisfactory cleaning instance and may determine and/or verify the satisfactory cleaning instance based on the received data from the second data processing platform 210.

In one example, the second data processing platform 210 may be configured to process and/or store second data from a plurality of devices 204. In one example, the second data processing platform 210 may store data from a group of devices 204 associated with a single location (e.g., a hospital, a fitness center, etc.) and/or a single organization (e.g., company, hospital group, medical offices, etc.) together in a datastore. Cleaning instance data associated with a particular location and/or a particular organization may be stored with an indication of association with the location and/or organization. In one example, the cleaning instance data associated with the particular location and/or particular organization may be stored in a single database shard, partition, etc.

Figure 3:
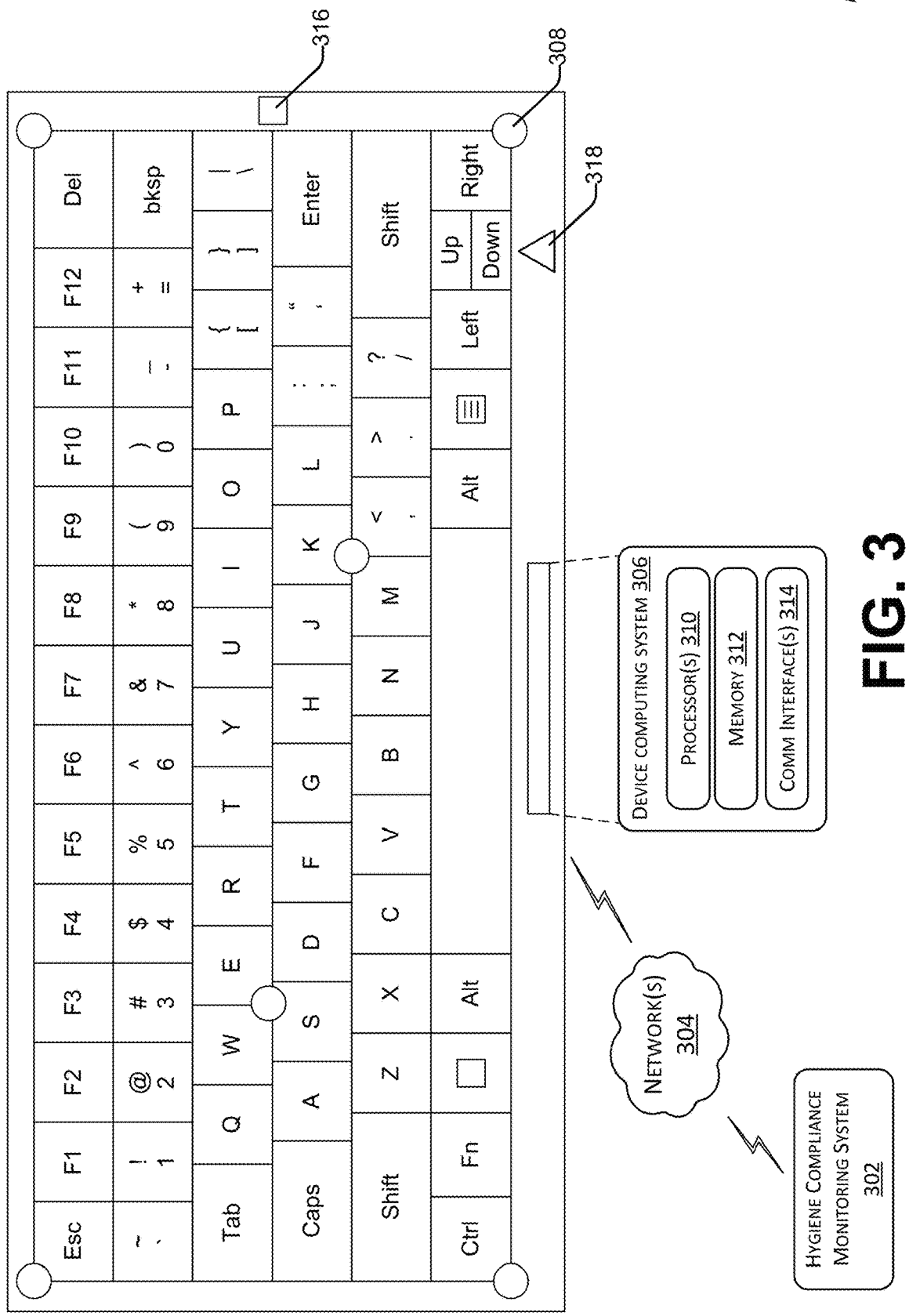
FIG. 3 illustrates an example device configured for detecting a cleaning instance and providing data associated therewith to a hygiene compliance monitoring system, as described herein.

FIG. 3 illustrates an example device 300 configured for detecting a cleaning instance and providing data associated therewith to a hygiene compliance monitoring system, as described herein. The device 300, such as computing device 102 and/or device 204 may include an input/output (I/O) device communicatively coupled to an associated computing device, such as computing device 214. In one example, the device 300 may include a portion of the associated computing device, such as a touchscreen or other interface configured for inputting data to the associated computing device. In some example, such as the keyboard example illustrated in FIG. 3, the device 300 may include a separate device that is configured to transmit data to the associated computing device via a wired and/or wireless connection.

As described herein, the device 300 may additionally be communicatively coupled to a hygiene compliance monitoring system 302, such as hygiene compliance monitoring system 104 of FIG. 1 and/or the second data processing platform 210 of FIG. 2 configured to monitor cleaning instances and satisfaction thereof associated with various devices. In one example, the device 300 and the hygiene compliance monitoring system 302 may be communicatively coupled via one or more network(s) 304, such as network(s) 108. In one example, the network(s) 304 may include a personal area network, such as Bluetooth® or the like. As described herein with respect to FIG. 2, a device computing system 306 (e.g., I/O device 120, computing device 214, etc.) of the device 300 may send cleaning instance data to the hygiene compliance monitoring system 302, such as for storage, cleanliness protocol monitoring, and/or the like.

In one example, the device computing system 306 may receive sensor data from one or more sensor(s) 308 of the device. The sensor(s) 308 may include pressure sensors, conductive sensors (e.g., conductive probes), capacitance sensors, humidity sensors, UV sensors, and/or the like. For example, the sensor(s) 308 may detect moisture on the surface of the device and may send sensor data associated with the detected moisture to the device computing system 306. In one example, one or more processor(s) 310 of the device computing system 306 may be configured to determine, based on the sensor data, whether the sensor data is associated with a cleaning instance. In one example, the processor(s) 310 may additionally be configured to determine whether a satisfactory cleaning instance occurred. The processor(s) 310 may be configured to determine, based on threshold data stored in memory 312, whether the sensor data satisfied one or more thresholds associated with a satisfactory cleaning instance.

In one example, the memory 312 may be configured to store cleaning instance data associated with one or more cleaning instances. In one example, the device computing system 306 may cause the data to be stored locally such as, for example, in the memory 312 until a condition associated with sending the data is satisfied. Non-limiting examples of the condition may include determining that a cleaning instance is complete, determining that a current time is associated with a time associated with sending the data, receiving a request to transmit cleaning instance data, and/or the like. For example, the device computing system 306 may be configured to transmit the cleaning instance data at periodic intervals (e.g., once per day, at 8 hour intervals, etc.). Based on a determination that a current time is associated with a periodic interval, the device computing system 306 may cause the cleaning instance data to be transmitted to the hygiene compliance monitoring system 302. In one example, the device computing system 306 may receive a request to transmit the cleaning instance data from the hygiene compliance monitoring system 302 such as, for example, a hygiene monitoring application running on a computing device associated with infection prevention personnel via a communication channel separate from the communication channel associated with transmitting the cleaning instance data. In response to the request, the device computing system 306 may transmit the cleaning instance data.

In one example, the device computing system 306 may include one or more communication interface(s) 314 configured to enable the device computing system 306 to communicate the cleaning instance data to the hygiene compliance monitoring system 302. The communication interface(s) 314 may include one or more interfaces and hardware components for enabling communication with various other devices over the network(s) 304 or directly. For example, the communication interface(s) 314 may enable Wi-Fi-based communication such as via frequencies defined by the IEEE 802.11 standards, short range wireless frequencies such as Bluetooth®, cellular communication (e.g., 2G, 2G, 4G, 4G LTE, 5G, etc.) or any suitable wired or wireless communications protocol that enables the respective computing device to interface with the other computing device(s).

As described herein, the cleaning instance data may include sensor data received from the sensor(s) 308 and/or sensor data received from additional sensor(s) 316, such as the additional sensor(s) 224. The additional sensor(s) 316 may include microphones, image capture devices (e.g., still frame and/or video images), motion detectors, and/or the like that are configured to capture the additional data in an environment of the device 300 and provide the additional data to the hygiene compliance monitoring system 302. Though illustrated as being included in the device 300, such as a component thereof, it is understood that the additional sensor(s) 316 may additionally or alternatively include sensor(s) that are communicatively coupled to the device 300, such as by a wired and/or wireless connection, such as sensors that are not configured to directly detect cleaning instance data.

In one example, and as enumerated herein, the device computing system 306 may send cleaning instance data and/or sensor data from the sensor(s) 308 and/or additional sensor(s) 316 to the hygiene compliance monitoring system 302 via a first communication channel (e.g., Bluetooth® communication channel) and may send other data associated with user input via the device 300 (e.g., user typing on keys of keyboard, inputting selections via a mouse function (e.g., clicks, movement on a trackpad, trackball, joystick, etc.), etc.) via a second communication channel that is independent of and different from the first communication channel. The device 300 may be configured to provide cleaning instance data via a separate communication channel, such as to enable the continuous separation of sensitive data input via the device 300 from cleaning instance data. By transmitting data via separate communication channels, the techniques described herein may improve the security of the sensitive data transmitted via the other communication channel, decreasing opportunities for a potential malicious attack on the sensitive data.

In one example, the device 300 may include a commercial off-the-shelf (COTS) I/O device, such as a standard keyboard. In one example, the device computing system 306 and/or other components thereof (e.g., sensor(s) 308, additional sensor(s) 316, etc.) may be provided as an add-on module configured to be coupled to the device 300. For example, the device computing system 306, sensor(s) 308 and/or additional sensor(s) 316, and/or a power system (e.g., batteries, etc.) may be incorporated into a plastic, silicone, rubber, and/or the like cover or overlay configured to couple to a COTS keyboard, providing the COTS keyboard with a protective layer to prevent pathogens from hiding in crevices, and additionally provide the functionality described herein. In one example, the device 300 may include a custom device configured with the components usable to perform the functions described herein.

The device 300 may further include one or more emitters 318. The emitters 318 may include, for example, a light, a speaker, a haptic device, a notification displayed on a user interface, and/or other device configured to emit light, sound, motion, and/or the like. As described herein, the emitters 318 may serve as a notification to the user as to when a cleaning instance is required, a satisfactory cleaning instance has been completed, other notifications, and combinations thereof.

In one example, the device 300 and/or various components thereof may be configured to receive power from one or more internal batteries configured to provide power to the device computing system 306, sensor(s) 308, additional sensor(s) 316, emitters, and/or the like. In one example, the device 300 may be configured to receive power via one or more Ethernet connections (e.g., Universal Serial Bus (USB), power over Ethernet (PoE)) such as via an existing connection between the device 300 and an associated computing device. In one example in which the device computing system 306 and/or other components associated therewith are configured in an add-on module, the add-on module may be coupled to the COTS device, such as to enable power transfer from the Ethernet connection associated with the COTS device to the device computing system 306 and/or other components associated therewith.

Figure 4:
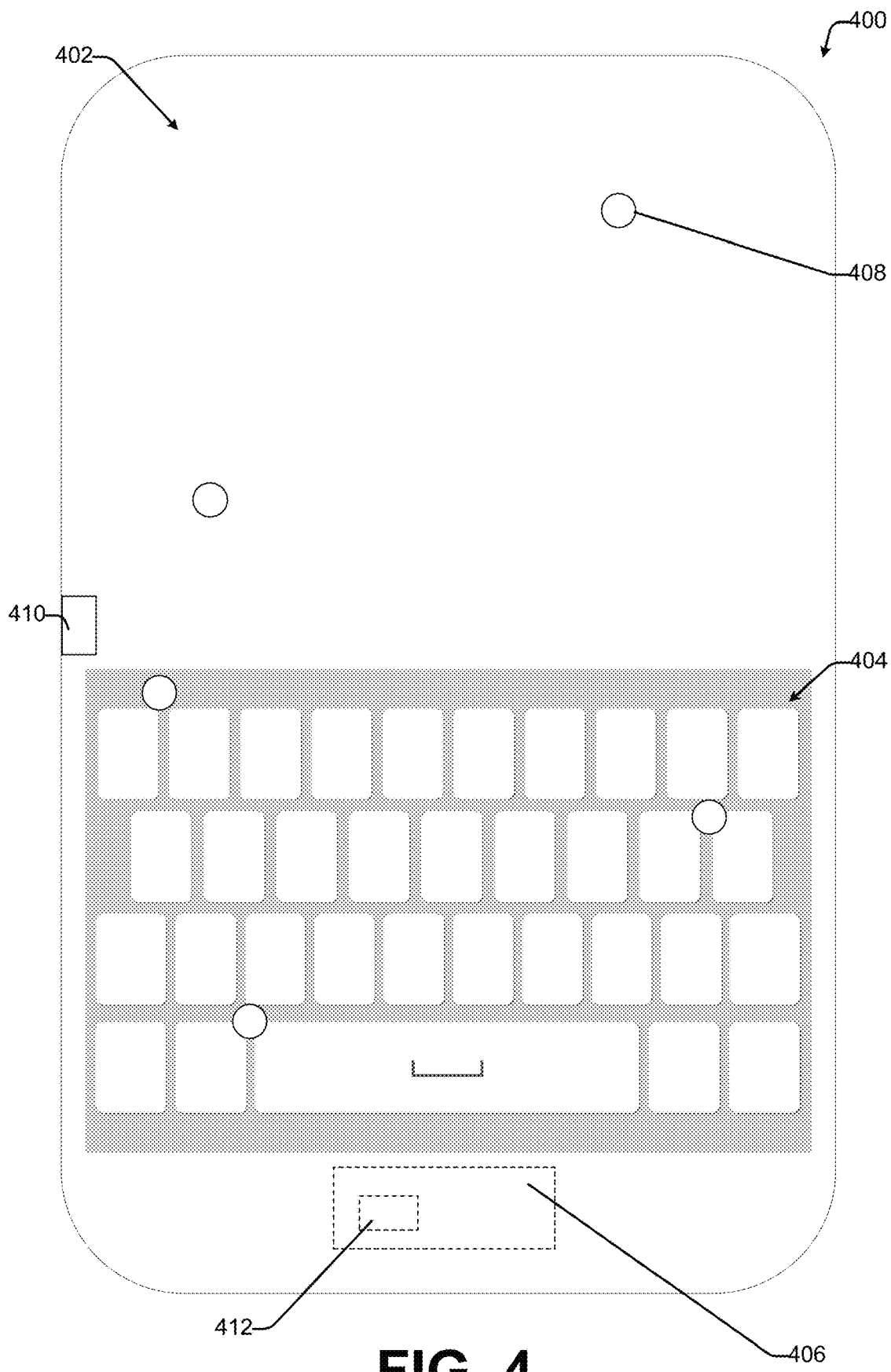
FIG. 4 illustrates an example device including a cleaning application configured to alert a user to clean the device according to a cleaning protocol, as described herein.

FIG. 4 illustrates an example device 400 including one or more application(s) 412 of a device computing system 406 configured to alert a user to clean the device 400 according to a cleaning protocol, as described herein. In one example, the device 400 may include a personal computing device, such as a smartphone, tablet, or other hand-held computing device configured for personal use. For example, the device 400 may include a physician's cell phone that may be operated in a hospital or medical office environment.

In one example, the application(s) 412 may include a native application or a web-based application configured to provide cleaning instance requirement data to the user 114. In one example, the cleaning instance requirement data may include a requirement to clean a surface of the device 400, such as with a cleansing wipe or other cleaning material. In one example, the cleaning instance requirement data may be determined based at least in part on a cleaning protocol, such as that provided by a hygiene compliance monitoring system 104, second data processing platform 210, hygiene compliance monitoring system 302, and/or the like. In one example, the application(s) 412 may be communicatively coupled to the cleanliness monitoring system to receive cleaning protocol data therefrom. In one example, the application(s) 412 may be configured to determine cleaning protocol data based on, for example, a location of the device 400. For example, the application(s) 412 may determine, based on location data (e.g., GPS data, cell data triangulation, wireless connections, etc.), that the device 400 is located in a hospital environment. Based on a determination that the device 400 is in the hospital environment, the application(s) 412 may determine an appropriate cleaning protocol (e.g., associated with the hospital, associated with a particular section of the hospital, etc.).

In one example, the application(s) 412 may provide an indication to the user to clean the device 400 based on the cleaning protocol. The indication may include any type of aural, visual, and/or haptic alert or notification. For example, the indication may include a vibration of the device 400 and/or a tone emitted from a speaker of the device (e.g., emitters 228 and 318). In one example, the indication may include a notification, such as a pop-up notification provided on a display of the device 400 and/or any other type of notification that may provide an indication to the user that a cleaning of the device 400 is required. In one example, the display of the device 400 may include a touchscreen 402. In one example, the touchscreen 402 may include any assembly of both an input ('touch panel') and output ('display') device.

In one example, the device 400 may include a commercial off-the-shelf computing device, such as a cell phone or smart phone purchased from a cellular service provider. In one example, the device 400 may be configured to detect the cleaning instance and provide data associated therewith to a hygiene compliance monitoring system 104 but may confirm a cleaning instance via different means due to the device 400 not being configured with the sensor(s) 308, additional sensor 316, and/or emitters 318 like the device 300 of FIG. 3. In one example, an alert may be provided to the user to clean the device 400 based on the cleaning protocol and may trust the user to comply with the cleaning protocol. In one example, the application(s) 412 may be configured to determine a cleaning instance based on input, from the user, via the application. In one example, the application(s) may detect a cleaning instance via, for example, the touchscreen 402 may detect a wiping motion across the surface of the touchscreen 402 indicative of a cleaning instance. Further, some smartphones may include humidity sensors used to detect whether the device 400 is submerged in water or an increase in humidity is significantly increased. This may indicate that a cleaning instance has occurred. In one example, once the cleaning instance has occurred, the device 400 may transmit cleaning instance data to a hygiene compliance monitoring system, such as hygiene compliance monitoring system 104 of FIG. 1 configured to monitor cleaning instances and satisfaction thereof associated with various devices. In one example, the device 400 and the hygiene compliance monitoring system 104 may be communicatively coupled via one or more networks, such as a cloud network, network, a cellular network, the Internet, other types of networks, and combinations thereof. As described herein with respect to FIG. 2, the device computing system 406 (e.g., I/O device 120, computing device 214, etc.) of the device 400 may send cleaning instance data to the hygiene compliance monitoring system 104, such as for storage, cleanliness protocol monitoring, and/or the like.

In one example, the device 400 may not be configured to detect the cleaning instance and provide data associated therewith to a hygiene compliance monitoring system since the device 400 of FIG. 4 may be a personal device used by a singular individual and very rarely handled by another individual. Thus, the application(s) 412 may provide the alert to the user to clean the device based on the cleaning protocol and may trust the user to comply with the cleaning protocol. In one example, the application(s) 412 may be configured to determine a cleaning instance based on input, from the user, via the application.

In one example, the user may launch or otherwise cause the application(s) 412 to be presented via the device and may select a cleaning mode and/or cleaning instance. In one example, the application(s) 412 may be given permissions by the device 400 to utilize sensors 408, additional sensor(s) 410, the touchscreen 402, motion sensors, environmental sensors, position sensors, ambient light sensors, proximity sensors, accelerometers, gyroscope sensors, barometers, compass sensors, pedometer sensors, and other sensors included in the device 400 (e.g., a smartphone) as a factory-installed sensor used in connection with any number of applications that may be executed on the device 400. By giving permissions to the application(s) 412, the user may utilize these factory-installed sensors to detect the cleaning instances. In one example, the application(s) 412 may be configured to detect motion, such as utilizing sensors associated with a touchscreen 402 of the device 400 that is indicative of a cleaning instance (e.g., cleaning motions, wiping motion, etc.). In one example, based on receiving an indication of selection of the cleaning mode, the application(s) 412 may temporarily disable the touchscreen 402 of the device 400, to enable the user to clean the device 400 without inadvertently inputting data.

In one example in which the device 400 does not include sensors 408, the application(s) 412 may be configured to determine the cleaning instance based on data received from one or more additional sensor(s) 410 that are associated with the device 400, as described above. For example, the additional sensor(s) 410 may include the touchscreen 402, a camera configured to capture one or more images of a cleaning motion and provide the sensor data associated therewith to the application(s) 412, and other additional sensor(s) 410. The application(s) 412 may receive the data and determine whether the cleaning instance is complete. In one example, the application(s) 412 may be configured to disable the cleaning mode after a threshold period of time (e.g., 5 seconds, 10 seconds, etc.). In one example, the application(s) 412 may cause the device 400 to disable the cleaning mode, and function as normal (e.g., processing input via the touchscreen 402, etc.). In one example, the application(s) 412 may receive a second input from the user (e.g., press of a button, second selection to exit the cleaning mode, etc.), and based on the second input, may disable the cleaning mode.

In one example, the device 400 may include one or more sensors 408 that are configured to detect input from the user (e.g., sensor data) and provide the sensor data to the application(s) 412 of the device computing system 406 for processing. In one example, the application(s) 412 may be configured determine whether a cleaning instance occurred and provide data associated with user input to the hygiene compliance monitoring system, as described herein. In the illustrative example, the device 400 includes a touchscreen 402, configured to detect the user input. In one example, the touchscreen 402 may include a keyboard 404, configured to enable the user to input text, symbols, numbers, and/or the like. In one example, the touchscreen 402 may be configured to enable the user to otherwise input data, such as via pre-populated menus (e.g., drop-down menus, etc.), and/or the like. In one example, the data input via the touchscreen 402 and/or the keyboard 404 may be transmitted to a data processing system, such as first data processing platform 206 of FIG. 2 and/or data processing system 106 of FIG. 1, via a first communication channel. The data entered via the touchscreen 402 and the keyboard 404 may define sensitive data and/or other data input via the computing devices such as data that is protected under laws and/or regulations (e.g., Health Insurance Portability and Accountability Act (HIPA Act), customer information, employee data, intellectual property, personal identifying information, etc.).

In one example, the application(s) 412 may be configured to store cleaning instance data associated with manually input and/or detected cleaning instances, such as in a datastore of the device 400. In one example, the device computing system 406 (e.g., via application(s) 412) may be configured to transmit cleaning instance data to a second data processing system, such as the second data processing platform 210 of FIG. 2 and/or hygiene compliance monitoring system 104 and/or 302, via a second communication channel. As described herein, the second communication channel may include a separate and independent communication channel from the first communication channel. The user input data transmitted to the data processing system may be transmitted via a different channel and maintained separate and apart from cleaning instance data transmitted via the second channel.

As described herein, the cleaning instance data may include a time, location, user data, and/or characteristics associated with a cleaning instance. In one example, the cleaning instance data may additionally or alternatively include sensor data received by the device computing system 406 from the sensor(s) 408 and/or the additional sensor(s) 410 associated with the device 400 (e.g., sensors 410 of the device 400 and/or located in an environment of the device 400).

Figure 5:
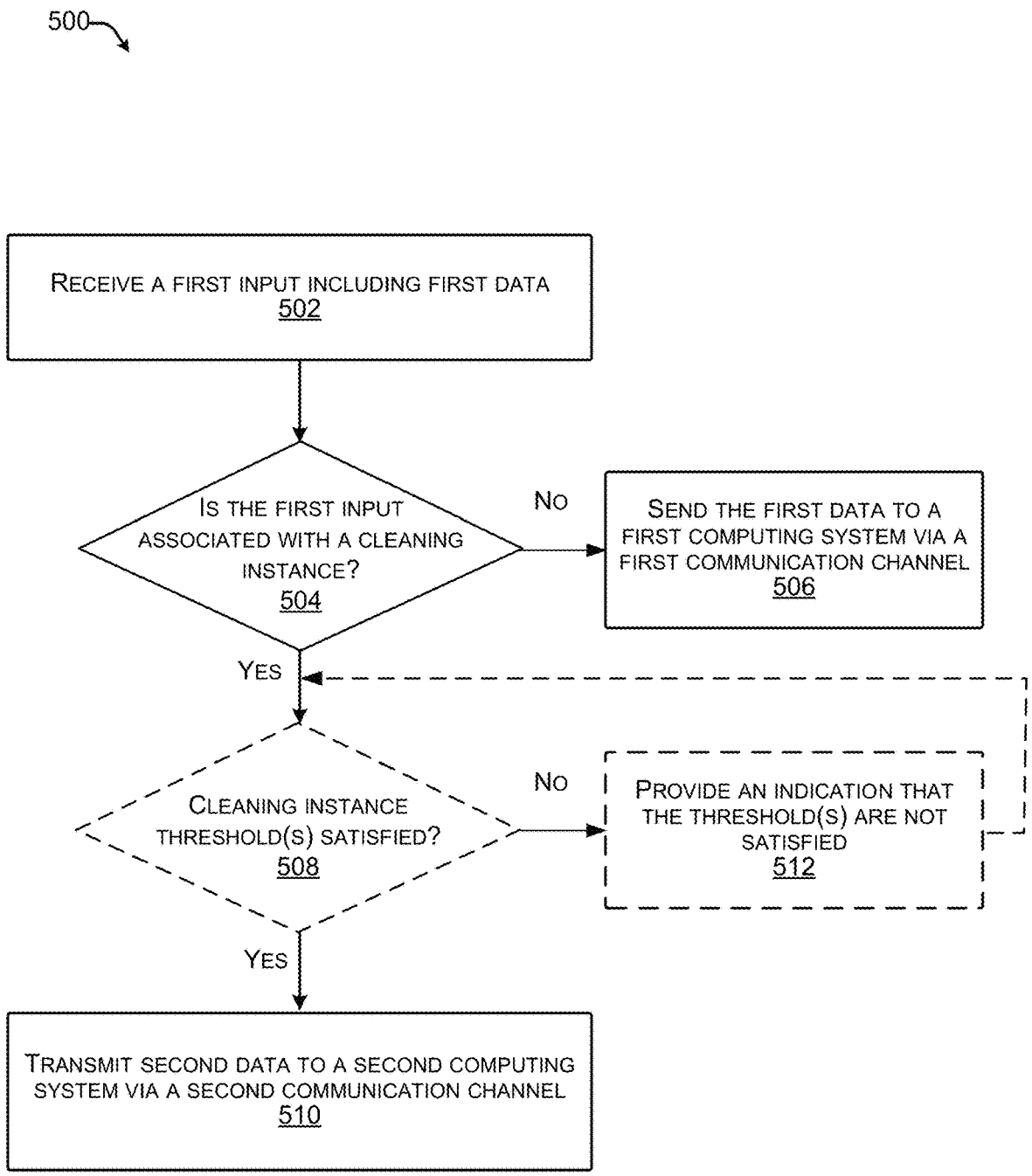
FIG. 5 illustrates an example process for providing hygiene compliance monitoring data to a hygiene compliance monitoring system, as described herein.

The process of FIG. 5 is illustrated as a collection of blocks in a logical flow diagram, which represent a sequence of operations, some or all of which may be implemented in hardware, software, or a combination thereof. In the context of software, the blocks may represent computer-executable instructions stored on one or more computer-readable media that, when executed by one or more processors, program the processors to perform the recited operations. The computer-executable instructions may include, for example, routines, programs, objects, components, data structures and the like that perform particular functions or implement particular data types. The order in which the blocks are described should not be construed as a limitation. Any number of the described blocks may be combined in any order and/or in parallel to implement the process, or alternative processes, and not all of the blocks need be executed. For discussion purposes, the process is described with reference to the environments, architectures and devices described in the examples herein, although the process may be implemented in a wide variety of other environments, architectures, and devices.

Various instructions, methods, and techniques described herein may be considered in the context of computer-executable instructions, such as, for example, program modules stored on computer-readable media, and executed by the processor(s) herein. The program modules may include, for example, routines, programs, objects, components, data structures, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

FIG. 5 illustrates an example process 500 for providing hygiene compliance monitoring data to a hygiene compliance monitoring system, as described herein. In one example, the operations described with respect to process 500 may be performed by one or more computing devices described herein, such as computing system 218 of device 204, device computing system 306 of device 300, and/or device computing system 406 of device 400.

At operation 502, the device computing system receives a first input including first data. In one example, the first data may include user input via an HMI interface associated with a device (e.g., an I/O device). In one example, the first data may include sensor data received from one or more sensors and/or one or more additional sensors. In one example, the device computing system may be configured to distinguish user input received via the HMI interface from sensor data, such as to keep data associated with each separate from one another. In one example, user input received via the HMI interface may not be processed by the device computing system, but instead may be transmitted directly to an associated computing device for processing.

At operation 504, the device computing system determines whether the first input is associated with a cleaning instance. In one example, the device computing system may determine that the first input is not associated with a cleaning instance (504, determination NO) based on a determination that the input is received via the HMI interface, such as text, symbols, numbers, selections, and/or the like input via the HMI interface. In one example, the device computing system may determine that the first input is an intelligible input (e.g., words input, distinct keystrokes, etc.) and not a swipe or multiple concurrent keystrokes associated with a wipe or other cleaning motion.

In one example, the device computing system may determine that the first input is associated with a cleaning instance (504, determination YES) based on a determination that the first input includes sensor data received from the sensors and/or additional sensors. In one example, the device computing system determines that the first input includes sensor data based on a determination that the sensor data satisfies one or more cleaning thresholds associated with a cleaning instances, as described above.

Based on a determination that the first input is not associated with a cleaning instance (504, determination NO), the device computing system, at operation 506, sends the first data to a first computing system via a first communication channel. The first computing system may include a computing device that is associated with the device (e.g., computing device corresponding to the I/O device). Additionally, in one example, the first computing system may include a data processing platform, such as the first data processing platform 206 of FIG. 2, configured to process and store the first data (e.g., sensitive data, data input via the device, etc.).

Based on a determination that the first input is associated with a cleaning instance (504, determination YES), the device computing system, at operation 508, may optionally determine whether one or more cleaning instance thresholds (e.g., cleaning instance criteria) are satisfied. The cleaning instance thresholds may include a threshold level of moisture, a threshold level of pressure, a threshold number of sweeping or other cleansing motions, a threshold amount of time (e.g., of the level of moisture, pressure, cleansing motions, etc.), a threshold percentage of surface cleaned, and/or the like, and combinations thereof. The cleaning instance threshold(s) may include minimum levels of cleansing criteria associated with a satisfactory cleaning instance. In one example, the cleaning instance threshold(s) may be determined based on one or more cleaning protocols, such as those set by an administrator based on an environment of the device. For example, the cleaning protocol(s) for a device located in a hospital setting may be different than cleaning protocol(s) associated with a device in a fitness center. For another example, the cleaning protocol(s) associated with a first department of a hospital (e.g., intensive care unit) may be different from cleaning protocols associated with a second department of the hospital (e.g., labor and delivery unit).

As described herein, the cleaning protocol(s) may be pre-programmed, such as in a memory of the device, and/or may be provided by a cleanliness monitoring system or cleaning data processing system located remote from and communicatively coupled to the device. In one example, the cleanliness monitoring system may provide data to the device via an associated computing device and/or via a direct communication connection that is separate from a second communication channel configured to transmit cleaning instance data from the device to the cleaning instance data, as described herein, such as in a one-way transmission of cleaning instance data.

In one example in which a determination associated with a satisfactory cleaning instance is not performed (e.g., optional operation 508 not performed), the device computing system may receive the sensor data and may, at operation 510, transmit the second data to a second computing system via a second communication channel (e.g., Bluetooth®). In one example, the second data may include cleaning instance data, such as sensor data received from the sensor(s) and/or the additional sensor(s).

In one example in which the device computing system determines whether a satisfactory cleaning is satisfied (508, determination YES), the device computing system transmits the second data including an indication that the cleaning instance threshold(s) are satisfied. In one example, the second data may include the sensor data, as described above, and/or post processing data, such as the percentage of surface cleaned, the amount of moisture and/or pressure detected, the amount of time that the moisture and/or pressure was detected, and/or other data associated with the cleaning instance determined by the device computing system based on the sensor data.

In one example, based on a determination that the cleaning instance threshold(s) are not satisfied (508, determination NO), the device computing system may optionally, at operation 512 provide an indication that the threshold(s) are not satisfied. As described herein, the device may include one or more emitters configured to emit a signal to a user to indicate that a cleaning instance is required and/or when the cleaning instance is satisfied. In one example, the emitter(s) may additionally be configured to provide an indication that the cleaning instance did not satisfy one or more thresholds (e.g., criteria) associated with a satisfactory cleaning instance. For example, the emitter may include a speaker that emits a signal indicating to the user to continue wiping a surface of the device to satisfy a cleaning instance.

In one example, after providing the indication, the device computing system may receive additional input associated with the cleaning instance and may again determine whether the cleaning instance threshold(s) are satisfied, as described with regard to operation 508. In one example, the device computing system may be configured to provide real-time and/or near real-time indicators to a user to inform the user as to a satisfaction of criteria associated with a cleaning instance. Accordingly, techniques described herein may be configured to ensure compliance with one or more cleaning protocols associated with an environment of the device.

Figure 6:
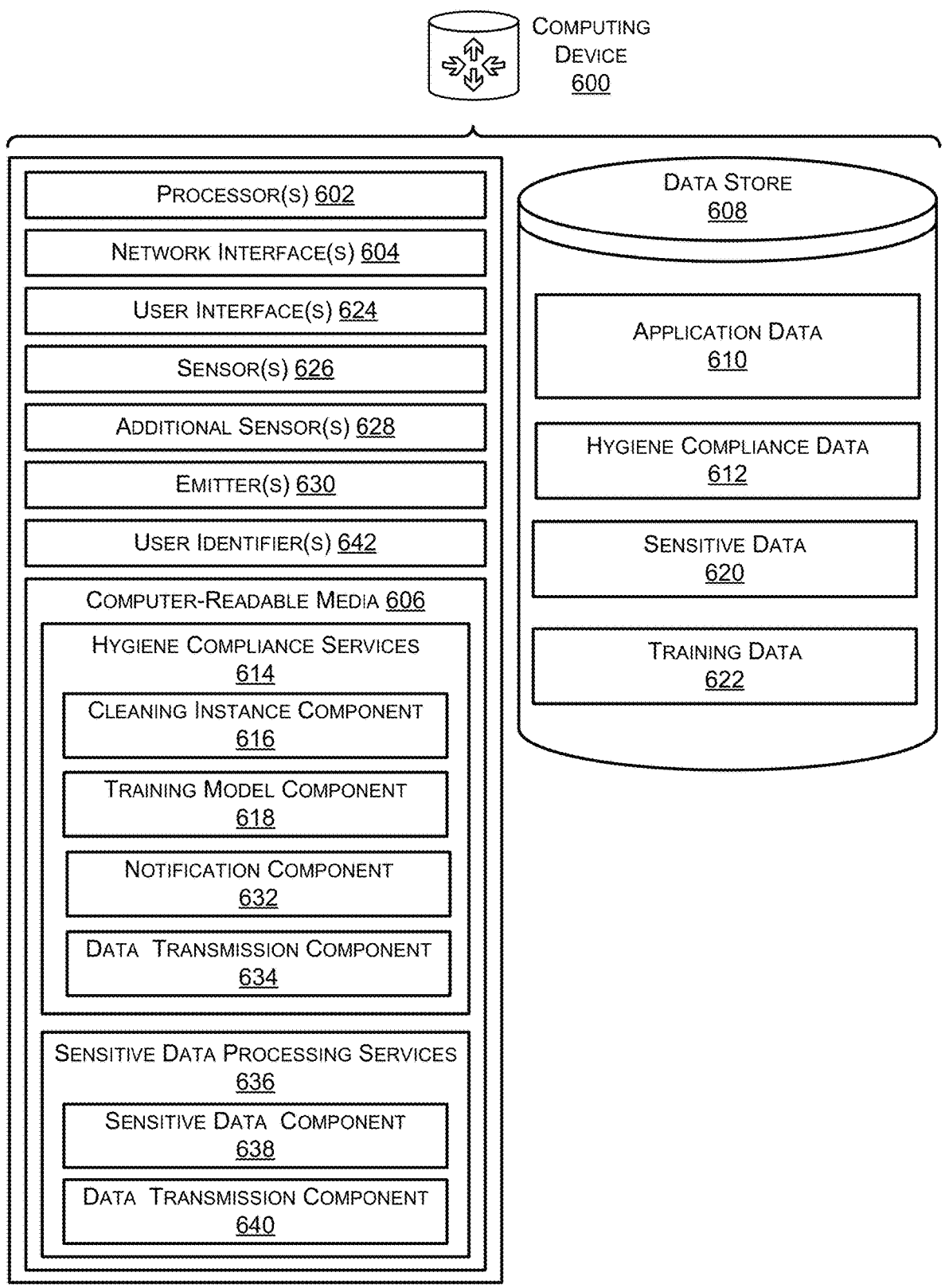
FIG. 6 is a component diagram of example components of a computing device including hygiene compliance services and sensitive data processing services, according to an example of the principles described herein.

FIG. 6 is a component diagram of example components of a computing device 600 including hygiene compliance services 614 and sensitive data processing services 636, according to an example of the principles described herein. The computing device 600 may include any of the computing devices describes herein including, for example, the computing devices 102 of FIG. 1, the device 204 and/or the computing system 218 of FIG. 2, the device 300 and/or the device computing system 306 of FIG. 3, and the device 400 and/or the device computing system 406 of FIG. 4.

As illustrated, the computing device 600 may include one or more hardware processor(s) 602 configured to execute one or more stored instructions. The processor(s) 602 may comprise one or more cores. Further, the computing device 600 may include one or more network interfaces 604 configured to provide communications between the computing device 600 and other devices, such as devices associated with the systems and devices of FIGS. 1 through 4 including the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices. The network interfaces 604 may include devices configured to couple to personal area networks (PANs), wired and wireless local area networks (LANs), wired and wireless wide area networks (WANs), and so forth. For example, the network interfaces 604 may include devices compatible with the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3 and/or other systems or devices associated with the computing device 600.

The computing device 600 may further include user interface(s) 624. The user interface(s) 624 may be any device associated with the computing device 600 (e.g., internal, external or remote from the computing device 600) via which a user may interact with the computing device 600 to exchange information between software, hardware, peripheral devices, the user, and combinations thereof. In one example, the user interface(s) 624 may be used to send data to the computing device 600, receive data from the computing device, and combinations thereof. In one example, the user interface(s) 624 may include a keyboard, a mouse, a touchpad, a joystick, a trackball, a touchscreen and/or other on-screen controllers, any other user interface, and combinations thereof.

The computing device 600 may further include one or more sensor(s) 626 configured to identify a cleaning instance and provide data associated therewith to the hygiene compliance monitoring system. Non-limiting examples of the sensor(s) 626 may include, for example, pressure sensors, conductive sensors (e.g., conductive probes), capacitance sensors, humidity sensors, ultra-violet (UV) sensors, other types of sensors, and combinations thereof. In one example, the sensor(s) may detect input associated with interaction with the computing device and may provide the input to the computing device. The computing device may include one or more processors configured to identify a cleaning instance associated with the interaction, such as from a detected amount of moisture on a surface of the I/O device (e.g., moisture associated with a cleaning wipe), detected movement associated with a cleansing gesture, and/or the like.

The computing device 600 may include one or more additional sensor(s) 628 configured to identify a cleaning instance and provide data associated therewith to the hygiene compliance monitoring system. The additional sensor(s) 628 may include microphones, image capture devices (e.g., still frame and/or video images), and/or the like that are configured to capture the additional data in an environment of the computing device and provide the additional data to the computing device 600. In one example, the additional sensor(s) 628 may be associated with the computing device 600 (e.g., a part of the computing device 600 as separate sensors) and/or may be remote sensors (e.g., independent of the computing device 600). In one example, the additional sensor(s) 628 may be configured to provide the additional data to the computing device 600 via a third communication channel 234, such as via a wired and/or wireless connection. Therefore, although depicted in FIG. 6 as being part of the computing device 600, the additional sensor(s) 628 may form part of the computing device 600, may be local to the computing device 600 but not form part of the computing device 600, may be remote from the computing device 600 but communicatively coupled to the computing device 600, and combinations thereof.

The computing device 600 may further include one or more emitter(s) 630. The emitter(s) 630 may include a light, a speaker, a haptic device, a notification displayed on the user interface(s) 624, and/or other device configured to emit light, sound, motion, and combinations thereof.

The computing device 600 may further include one or more user identifier(s) 642. In one example, the user identifier(s) 642 may include a card reader used to read an identification card identifying a user associated with the computing device 600 and/or a user associated with a cleaning instance of the computing device 600 and/or the user interface(s) 624. In one example, the user identifier(s) 642 may include login hardware and/or software via which a user may enter credentials (e.g., a username, a password, an authentication code, and combinations thereof) to identify a user associated with the computing device 600 and/or a user associated with a cleaning instance of the computing device 600 and/or the user interface(s) 624.

The computing device 600 may also include computer-readable media 606 that stores various executable components (e.g., software-based components, firmware-based components, etc.). In one example, the computer-readable media 606 may include, for example, working memory, random access memory (RAM), read only memory (ROM), and other forms of persistent, non-persistent, volatile, non-volatile, and other types of data storage. In addition to various components discussed herein, the computer-readable media 606 may further store components to implement functionality described herein. While not illustrated, the computer-readable media 606 may store one or more operating systems utilized to control the operation of the one or more devices that comprise the computing device 600. According to one example, the operating system comprises the LINUX operating system. According to another example, the operating system(s) comprise the WINDOWS SERVER operating system from MICROSOFT Corporation of Redmond, Washington According to further examples, the operating system(s) may comprise the UNIX operating system or one of its variants. It may be appreciated that other operating systems may also be utilized.

Additionally, the computing device 600 may include a data store 608 which may comprise one, or multiple, repositories or other storage locations for persistently storing and managing collections of data such as databases, simple files, binary, and/or any other data. The data store 608 may include one or more storage locations that may be managed by one or more database management systems. The data store 608 may store, for example, application data 610 defining computer-executable code utilized by the processor 602 to execute hygiene compliance services 614 and/or the sensitive data processing services 636. Further, the application data 610 may include data relating to user preferences associated with the hygiene compliance data, the sensitive data, and other data that may be used by the execute hygiene compliance services 614 and/or the sensitive data processing services 636 to perform the functions described herein.

Further, the data store 608 may store the hygiene compliance data 612. The hygiene compliance data 612 may include any data associated with one or more cleaning instances of the computing device 600 as described herein. The hygiene compliance data 612 may include, for example, a time, location, and/or user 114 associated with a particular cleaning instance as described herein.

The data store 608 may store the sensitive data 620. The sensitive data 620 may include any data that is protected under laws and/or regulations (e.g., Health Insurance Portability and Accountability Act, customer information, employee data, intellectual property, personal identifying information, etc.) or any data that may include personal or private information. In one example, the sensitive data 620 may include the health data 112 of FIG. 1.

The data store 608 may further store training data 622. The training data 622 may include any data used to train a threshold determination system associated with the user interface(s) 624 of the computing device 600. In one example, the training data 622 may include any data used by an artificial intelligence (AI) program, a machine learning (ML) program, other computer program, and combinations thereof to train, for example, a threshold determination system associated with the user interface(s) 624 of the computing device 600.

The computer-readable media 606 may store portions, or components, of the hygiene compliance services 614 and the sensitive data processing services 636. For example, the hygiene compliance services 614 of the computer-readable media 606 may include a cleaning instance component 616 to, when executed by the processor(s) 602, perform the identification of a cleaning instance of the computing device 600 and any component thereof including, for example, the user interface(s) 624. The cleaning instance component 616 may, when executed by the processor(s) 602, identify, for example, times associated with the cleaning instance (start time, stop time, etc.), location associated with the cleaning instance, a user associated with the cleaning instance, percentage of surface cleaned, satisfaction (or not) of criteria associated with a cleaning instance (e.g., level of moisture, pressure, etc. satisfies one or more thresholds, percentage of surface cleaned satisfies a threshold, etc.), other cleaning instance information, and combinations thereof. The cleaning instance component 616 may further include a threshold determination system as described herein to allow for a number of threshold levels of cleaning has occurred to a satisfactory level or is satisfactory in general. The cleaning instance component 616 may further produce the hygiene compliance data 612 described herein.

The hygiene compliance services 614 of the computer-readable media 606 may also include a training model component 618. The training model component 618 may, when executed by the processor(s) 602, train the threshold determination system of the cleaning instance component 616 associated with a user interface of the computing device 600. The threshold determination system may associate one or more thresholds with the user interface of the computing device 600 such as to determine whether a cleaning instance was satisfactory. As described herein, the thresholds may be associated with moisture level, pressure applied, time associated with a cleaning instance, other standards, and combinations thereof. In one example, the training model component 618 may receive, as an input one or more inputs associated with a training cleaning instance. In one example, the training model component 618 may be configured to receive the input and identify one or more thresholds (e.g., moisture level, capacitance detected, time associated with the capacitance, time of decay of capacitance, pressure detected, etc.) based on the input. In one example, the training model component 618 may utilize the training data 622 to perform the functions of the training model component 618. The training model component 618 may then set the thresholds associated with a satisfactory cleaning instance based on the input. Further, the training model component 618 may further perform other types of training of the computing device 600 and may utilize an artificial intelligence (AI) program, a machine learning (ML) program, other computer program, and combinations thereof to train the computing device 600 to perform one or more functions described herein.

The hygiene compliance services 614 of the computer-readable media 606 may also include a notification component 632. The notification component 632 may, when executed by the processor(s) 602, notify a user via a number of activations of the emitter(s) 630. The notifications produced by the notification component 632 may include, for example, notifications regarding the need to clean the computing device 600, the user interface(s) 624 thereof, other elements of the computing device 600, and combinations thereof. The notifications produced by the notification component 632 may further include notifications regarding a contamination instance wherein a contaminant is spilled or otherwise placed on the computing device 600, the user interface(s) 624 thereof, other elements of the computing device 600, and combinations thereof. The notifications produced by the notification component 632 may further include notifications regarding the completion and/or a satisfactory level of cleanliness having been obtained. The notification component 632 may produce any number of notifications as described herein.

The hygiene compliance services 614 of the computer-readable media 606 may also include a data transmission component 634. The data transmission component 634 may, when executed by the processor(s) 602, cause the hygiene compliance data 612 produced by the cleaning instance component 616 and stored in the data store 608 to be transmitted to a device communicatively coupled to the computing device 600. For example, the data transmission component 634 may transmit the hygiene compliance data 612 to the hygiene compliance monitoring system 104 as the cleaning instance data 110 as depicted and described herein in connection with FIG. 1. Further, in one example, the data transmission component 634 may transmit the hygiene compliance data 612 to the hub/repeater 230, the IoT gateway 232, and/or the second data processing platform as depicted and described herein in connection with FIG. 2. Still further, the data transmission component 634 may transmit the hygiene compliance data 612 to the hygiene compliance monitoring system 302 as depicted and described herein in connection with FIG. 3.

The computer-readable media 606 may store portions, or components, of the sensitive data processing services 636. For example, the sensitive data processing services 636 of the computer-readable media 606 may include a sensitive data component 638 to, when executed by the processor(s) 602, detect entry of sensitive data into the user interface(s) 624 of the computing device 600. The sensitive data component 638 may also, when executed by the processor(s) 602, aggregate, process and or store the sensitive data 620 within the data store 608.

The sensitive data processing services 636 of the computer-readable media 606 may also include a data transmission component 640. The data transmission component 640 may, when executed by the processor(s) 602, cause the sensitive data 620 produced by the sensitive data component 638 and stored in the data store 608 to be transmitted to a device communicatively coupled to the computing device 600. For example, the data transmission component 640 may transmit the sensitive data 620 to the data processing system 106 as the health data 112 as depicted and described herein in connection with FIG. 1. Further, the data transmission component 640 may transmit the sensitive data 620 to the computing device 214, the access control system 216, and/or the first data processing platform 206 as depicted and described herein in connection with FIG. 2.

Figure 7:
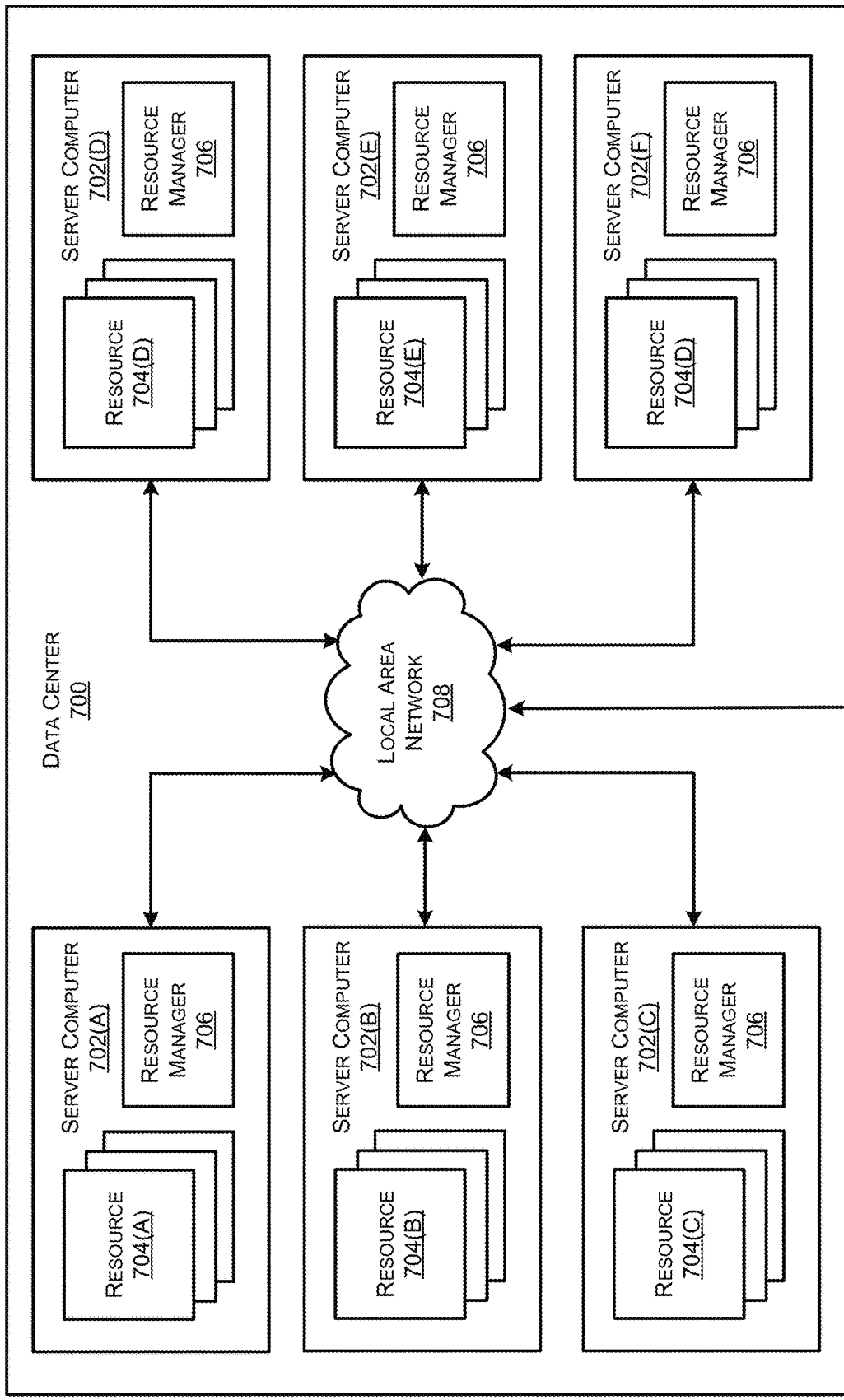
FIG. 7 illustrates a computing system diagram illustrating a configuration for a data center 700 that may be utilized to implement aspects of the technologies disclosed herein.

FIG. 7 illustrates a computing system diagram illustrating a configuration for a data center 700 that may be utilized to implement aspects of the technologies disclosed herein. The example data center 700 shown in FIG. 7 includes several server computers 702A-702F (which might be referred to herein singularly as "a server computer 702" or in the plural as "the server computers 702) for providing computing resources. In some examples, the resources and/or server computers 702 may include, or correspond to, any type of networked device described herein. Although described as servers, the server computers 702 may comprise any type of networked device, such as servers, switches, routers, hubs, bridges, gateways, modems, repeaters, access points, etc.

The server computers 702 may be standard tower, rackmount, or blade server computers configured appropriately for providing computing resources. In some examples, the server computers 702 may provide computing resources 704 including data processing resources such as VM instances or hardware computing systems, database clusters, computing clusters, storage clusters, data storage resources, database resources, networking resources, virtual private networks (VPNs), and others. Some of the server computers 702 may also be configured to execute a resource manager 706 capable of instantiating and/or managing the computing resources. In the case of VM instances, for example, the resource manager 706 may be a hypervisor or another type of program configured to enable the execution of multiple VM instances on a single server computer 702. Server computers 702 in the data center 700 may also be configured to provide network services and other types of services.

In the example data center 700 shown in FIG. 7, an appropriate LAN 708 is also utilized to interconnect the server computers 702A-702F. It may be appreciated that the configuration and network topology described herein has been greatly simplified and that many more computing systems, software components, networks, and networking devices may be utilized to interconnect the various computing systems disclosed herein and to provide the functionality described above. Appropriate load balancing devices or other types of network infrastructure components may also be utilized for balancing a load between data centers 700, between each of the server computers 702A-702F in each data center 700, and, potentially, between computing resources in each of the server computers 702. It may be appreciated that the configuration of the data center 700 described with reference to FIG. 7 is merely illustrative and that other implementations may be utilized.

In some examples, the server computers 702 and or the computing resources 704 may each execute/host one or more tenant containers and/or virtual machines to perform techniques described herein.

In some instances, the data center 700 may provide computing resources, like tenant containers, VM instances, VPN instances, and storage, on a permanent or an as-needed basis. Among other types of functionality, the computing resources provided by a cloud computing network may be utilized to implement the various services and techniques described herein. The computing resources 704 provided by the cloud computing network may include various types of computing resources, such as data processing resources like tenant containers and VM instances, data storage resources, networking resources, data communication resources, network services, VPN instances, and the like.

Each type of computing resource 704 provided by the cloud computing network may be general-purpose or may be available in a number of specific configurations. For example, data processing resources may be available as physical computers or VM instances in a number of different configurations. The VM instances may be configured to execute applications, including web servers, application servers, media servers, database servers, some or all of the network services described above, and/or other types of programs. Data storage resources may include file storage devices, block storage devices, and the like. The cloud computing network may also be configured to provide other types of computing resources 704 not mentioned specifically herein.

The computing resources 704 provided by a cloud computing network may be enabled in one example by one or more data centers 700 (which might be referred to herein singularly as "a data center 700" or in the plural as "the data centers 700). The data centers 700 are facilities utilized to house and operate computer systems and associated components. The data centers 700 typically include redundant and backup power, communications, cooling, and security systems. The data centers 700 may also be located in geographically disparate locations. One illustrative example for a data center 700 that may be utilized to implement the technologies disclosed herein is described herein with regard to, for example, FIGS. 1 through 6.

Figure 8:
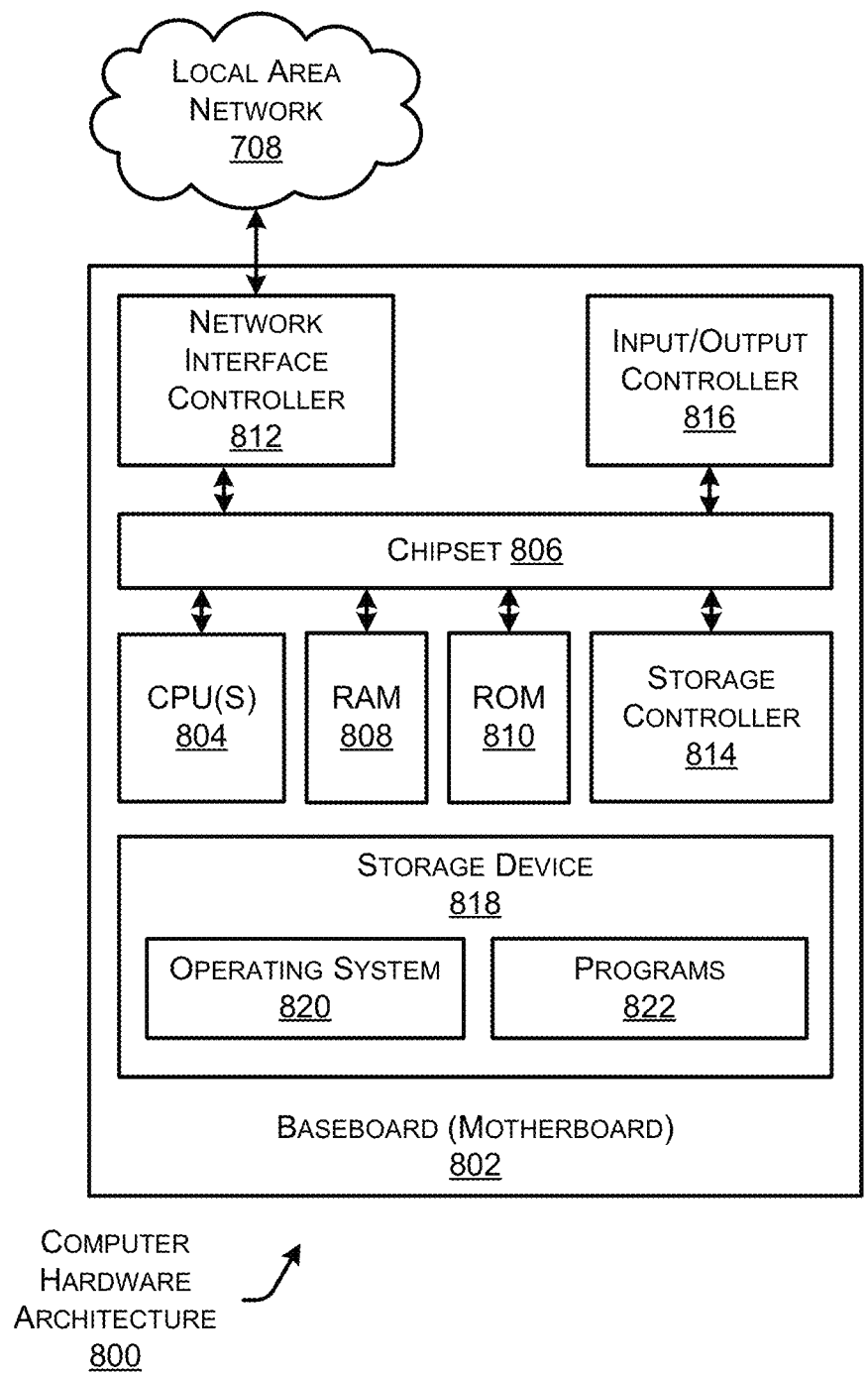
FIG. 8 illustrates a computer architecture diagram showing an example computer hardware architecture for implementing a computing device that may be utilized to implement aspects of the various technologies presented herein.

FIG. 8 illustrates a computer architecture diagram showing an example computer hardware architecture 800 for implementing a computing device that may be utilized to implement various aspects of the various technologies presented herein. The computer hardware architecture 800 shown in FIG. 8 illustrates the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices, a workstation, a desktop computer, a laptop, a tablet, a network appliance, an e-reader, a smartphone, or other computing device, and may be utilized to execute any of the software components described herein. The computer 800 may, in some examples, correspond to a network device (e.g., computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices (and associated devices) described herein, and may comprise networked devices such as servers, switches, routers, hubs, bridges, gateways, modems, repeaters, access points, etc.

The computer 800 includes a baseboard 802, or "motherboard," which is a printed circuit board to which a multitude of components or devices may be connected by way of a system bus or other electrical communication paths. In one illustrative configuration, one or more central processing units (CPUs) 804 operate in conjunction with a chipset 806. The CPUs 804 may be standard programmable processors that perform arithmetic and logical operations necessary for the operation of the computer 800.

The CPUs 804 perform operations by transitioning from one discrete, physical state to the next through the manipulation of switching elements that differentiate between and change these states. Switching elements generally include electronic circuits that maintain one of two binary states, such as flip-flops, and electronic circuits that provide an output state based on the logical combination of the states of one or more other switching elements, such as logic gates. These basic switching elements may be combined to create more complex logic circuits, including registers, adders-subtractors, arithmetic logic units, floating-point units, and the like.

The chipset 806 provides an interface between the CPUs 804 and the remainder of the components and devices on the baseboard 802. The chipset 806 may provide an interface to a RAM 808, used as the main memory in the computer 800. The chipset 806 may further provide an interface to a computer-readable storage medium such as a read-only memory (ROM) 810 or non-volatile RAM (NVRAM) for storing basic routines that help to startup the computer 800 and to transfer information between the various components and devices. The ROM 810 or NVRAM may also store other software components necessary for the operation of the computer 800 in accordance with the configurations described herein.

The computer 800 may operate in a networked environment using logical connections to remote computing devices and computer systems through a network, such as the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices, among other devices. The chipset 806 may include functionality for providing network connectivity through a Network Interface Controller (NIC) 812, such as a gigabit Ethernet adapter. The NIC 812 is capable of connecting the computer 800 to other computing devices within the LAN 708 and external to the LAN 708. It may be appreciated that multiple NICs 812 may be present in the computer 800, connecting the computer to other types of networks and remote computer systems. In some examples, the NIC 812 may be configured to perform at least some of the techniques described herein, such as packet redirects and/or other techniques described herein.

The computer 800 may be connected to a storage device 818 that provides non-volatile storage for the computer. The storage device 818 may store an operating system 820, programs 822 (e.g., any computer-readable and/or computer-executable code described herein), and data, which have been described in greater detail herein. The storage device 818 may be connected to the computer 800 through a storage controller 814 connected to the chipset 806. The storage device 818 may consist of one or more physical storage units. The storage controller 814 may interface with the physical storage units through a serial attached SCSI (SAS) interface, a serial advanced technology attachment (SATA) interface, a fiber channel (FC) interface, or other type of interface for physically connecting and transferring data between computers and physical storage units.

The computer 800 may store data on the storage device 818 by transforming the physical state of the physical storage units to reflect the information being stored. The specific transformation of physical state may depend on various factors, in different examples of this description. Examples of such factors may include, but are not limited to, the technology used to implement the physical storage units, whether the storage device 818 is characterized as primary or secondary storage, and the like.

For example, the computer 800 may store information to the storage device 818 by issuing instructions through the storage controller 814 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 800 may further read information from the storage device 818 by detecting the physical states or characteristics of one or more particular locations within the physical storage units.

In addition to the storage device 818 described above, the computer 800 may have access to other computer-readable storage media to store and retrieve information, such as program modules, data structures, or other data. It may be appreciated by those skilled in the art that computer-readable storage media is any available media that provides for the non-transitory storage of data and that may be accessed by the computer 800. In some examples, the operations performed by the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices, and or any components included therein, may be supported by one or more devices similar to computer 800. Stated otherwise, some or all of the operations performed by the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices, and or any components included therein, may be performed by one or more computer devices operating in a cloud-based arrangement.

By way of example, and not limitation, computer-readable storage media may include volatile and non-volatile, removable and non-removable media implemented in any method or technology. Computer-readable storage media includes, but is not limited to, RAM, ROM, erasable programmable ROM (EPROM), electrically-erasable programmable ROM (EEPROM), flash memory or other solid-state memory technology, compact disc ROM (CD-ROM), digital versatile disk (DVD), high definition DVD (RD-DVD), BLU-RAY, or other optical storage, magnetic cassettes, magnetic tape, magnetic disk storage or other magnetic storage devices, or any other medium that may be used to store the desired information in a non-transitory fashion.

As mentioned briefly above, the storage device 818 may store an operating system 820 utilized to control the operation of the computer 800. According to one example, the operating system 820 comprises the LINUX operating system. According to another example, the operating system comprises the WINDOWS® SERVER operating system from MICROSOFT Corporation of Redmond, Washington According to further examples, the operating system may comprise the UNIX operating system or one of its variants. It may be appreciated that other operating systems may also be utilized. The storage device 818 may store other system or application programs and data utilized by the computer 800.

In one example, the storage device 818 or other computer-readable storage media is encoded with computer-executable instructions which, when loaded into the computer 800, transform the computer from a general-purpose computing system into a special-purpose computer capable of implementing the examples described herein. These computer-executable instructions transform the computer 800 by specifying how the CPUs 804 transition between states, as described above. According to one example, the computer 800 has access to computer-readable storage media storing computer-executable instructions which, when executed by the computer 800, perform the various processes described above with regard to FIGS. 1 through 7. The computer 800 may also include computer-readable storage media having instructions stored thereupon for performing any of the other computer-implemented operations described herein.

The computer 800 may also include one or more input/output controllers 816 for receiving and processing input from a number of input devices, such as a keyboard, a mouse, a touchpad, a touchscreen, an electronic stylus, or other type of input device. Similarly, an input/output controller 816 may provide output to a display, such as a computer monitor, a flat-panel display, a digital projector, a printer, or other type of output device. It will be appreciated that the computer 800 might not include all of the components shown in FIG. 8, may include other components that are not explicitly shown in FIG. 8, or might utilize an architecture completely different than that shown in FIG. 8.

As described herein, the computer 800 may comprise one or more of the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices. The computer 800 may include one or more hardware processor(s) such as the CPUs 804 configured to execute one or more stored instructions. The CPUs 804 may comprise one or more cores. Further, the computer 800 may include one or more network interfaces configured to provide communications between the computer 800 and other devices, such as the communications described herein as being performed by the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices, and other devices described herein. The network interfaces may include devices configured to couple to personal area networks (PANs), wired and wireless local area networks (LANs), wired and wireless wide area networks (WANs), and so forth. For example, the network interfaces may include devices compatible with Ethernet, Wi-Fi™, and so forth.

The programs 822 may comprise any type of programs or processes to perform the techniques described in this disclosure for the computing devices 102 of FIG. 1, the device 204 and/or the computing system 218 of FIG. 2, the device 300 and/or the device computing system 306 of FIG. 3, and the device 400 and/or the device computing system 406 of FIG. 4, the hygiene compliance monitoring system 104 and/or the data processing system 106 of FIG. 1, the computing device 214, the access control system 216, the first data processing platform 206, the hub/repeater 230, the IoT gateway 232, and/or the second data processing platform of FIG. 2, the hygiene compliance monitoring system 302 of FIG. 3, and/or other systems or devices associated with the above-listed computing devices and/or remote from the above-listed computing devices as described herein. The programs 822 may enable the devices described herein to perform various operations.

CONCLUSION

Although the discussion above sets forth example implementations of the described techniques, other architectures may be used to implement the described functionality and are intended to be within the scope of this disclosure. For example, though primarily discussed herein as a system associated with a keyboard, such as a USB keyboard associated with a personal computer, the concepts described herein are configured to be associated with any type of HMI device equipped with a cleanliness monitor, including but not limited to computer mice, keyboards, touchscreens, touchscreen accessories, desktop telephones, and/or the like.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:
1. A human-machine interface (HMI) device comprising:
   an interface configured to convert user input into an electronic signal;
   a sensor configured to detect a state of cleanliness of the interface;

one or more processors; and
one or more computer-readable media storing instructions that, when executed by the one or more processors, cause the processors to transmit:
first data via a primary communication channel between the HMI device and an associated endpoint based at least in part on the first data including sensitive information, the primary communication channel being determined from a multitude of communication channels such that the primary communication channel transmits a limited amount of non-sensitive information in a manner that enhances security of the associated endpoint, and
second data via a secondary communication channel between the HMI device and an external computing system based at least in part on the second data including cleaning action information, the secondary communication channel being determined from the multitude of communication channels such that the secondary communication channel transmits a limited amount of sensitive information in a manner that saves processing power of the external computing system.

2. The HMI device of claim 1, wherein the interface includes at least one of a keyboard, a mouse, a touchpad, a joystick, a trackball, a telephone, a touchscreen, or an accessory associated with the touchscreen.

3. The HMI device of claim 1, wherein the first data further includes user-generated data.

4. The HMI device of claim 1, wherein the first data includes one or more of Health Insurance Portability and Accountability Act (HIPA Act) associated data, customer information data, employee data, data defining intellectual property, or data defining personal identifying information.

5. The HMI device of claim 1, wherein the sensor includes at least one of: a pressure sensor, a conductive sensor, a capacitance sensor, a humidity sensor, an ultra-violet (UV) sensor, a microphone, or an image capture device.

6. The HMI device of claim 1, wherein the sensor is configured to detect an input associated with a user interaction with the HMI device.

7. The HMI device of claim 1, wherein the sensor is configured to detect a change in an environment of the HMI device, and
wherein the change in the environment includes one or more of: a change in humidity, a change in ambient electromagnetic waves, a change in pressure applied to the HMI device, a change in electromagnetic conductance at the HMI device, a change in acoustic wavelengths, a change in acoustic frequencies, or a change in motion around the HMI device.

8. The HMI device of claim 1, further comprising a device identifier associated with the HMI device, the device identifier identifying the HMI device with a cleaning instance to a hygiene compliance monitoring system.

9. The HMI device of claim 1, further comprising a user identifier to identify a user of the HMI device to a hygiene compliance monitoring system,
wherein the user identifier comprises user credentials used to identify the user who is cleaning the HMI device.

10. A method of a human-machine interface (HMI) device securing sensitive data and hygiene compliance data, the method comprising:
receiving a user input at an interface of the HMI device;
determining first data associated with the user input, the first data including an indication of sensitive information;
determining second data associated with the user input, the second data including an indication of cleaning action information of a cleaning instance of one or more portions of a computing device;
transmitting the first data to a first computing system via a first communication channel based, at least in part, on the first data including the indication of the sensitive information, the first communication channel being determined from a multitude of communication channels such that the first communication channel transmits a limited amount of non-sensitive information in a manner that enhances security of the first computing system; and
transmitting second data to a second computing system via a second communication channel that is different from the first communication channel based, at least in part, on the second data including the indication of the cleaning action information of the cleaning instance, the second communication channel being determined from the multitude of communication channels such that the second communication channel transmits a limited amount of sensitive information in a manner that saves processing power of the second computing system.

11. The method of claim 10, further comprising:
determining whether one or more cleaning instance thresholds are reached;
based, at least in part, on the one or more cleaning instance thresholds not being reached, providing an indication that the one or more cleaning instance thresholds are not reached; and
based, at least in part, on the one or more cleaning instance thresholds being reached, providing an indication that the one or more cleaning instance thresholds are reached, transmitting the second data to the second computing system via the second communication channel.

12. The method of claim 11, wherein the one or more cleaning instance thresholds include: a threshold level of moisture, a threshold level of pressure, a threshold number of cleansing motions, a threshold amount of time, or a threshold percentage of surface cleaned.

13. The method of claim 12, wherein the one or more cleaning instance thresholds are determined based on one or more cleaning protocols.

14. The method of claim 10, further comprising alerting a user to clean one or more portions of the computing device.

15. The method of claim 10, wherein the indication of the cleaning action information includes one of:
an indication that a cleaning action was completed, or
an indication that the cleaning action is needed.

16. A non-transitory computer-readable medium storing instructions that, when executed, causes a processor to perform operations, comprising:
transmitting first data via a primary communication channel between a human-machine interface (HMI) device and an associated endpoint based at least in part on the first data including sensitive information, the primary communication channel being determined from a multitude of communication channels such that the primary communication channel transmits a limited amount of non-sensitive information in a manner that enhances security of the associated endpoint; and
transmitting second data via a secondary communication channel between the HMI device and an external computing system based at least in part on the second data including cleaning action information, the secondary communication channel being determined from the multitude of communication channels such that the secondary communication channel transmits a limited amount of sensitive information in a manner that saves processing power of the external computing system.

17. The non-transitory computer-readable medium of claim 16, the operations further comprising:
   detecting, via one or more sensors:
   a clean state of the HMI device;
   a dirty state of the HMI device; or
   a cleaning instance associated with the HMI device; and
   alerting a user to clean one or more portions of the HMI device.

18. The non-transitory computer-readable medium of claim 16, the operations further comprising:
   determining whether a non-cleaning interaction has occurred with respect to the HMI device; and
   based at least in part on the non-cleaning interaction having occurred, withholding transmission of data associated with the non-cleaning interaction.

19. The non-transitory computer-readable medium of claim 16, the operations further comprising:
   determining whether one or more cleaning instance thresholds are satisfied reached;
   based, at least in part, on the one or more cleaning instance thresholds not being reached, providing an indication that the one or more cleaning instance thresholds are not reached; and
   based, at least in part, on the one or more cleaning instance thresholds being reached, providing an indication that the one or more cleaning instance thresholds are reached, transmitting the second data to a second computing system via the secondary communication channel.

20. The non-transitory computer-readable medium of claim 16, wherein the cleaning action information includes one of:
   an indication that a cleaning action was completed, or
   an indication that the cleaning action is needed.

* * * * *